(12) United States Patent
Liu

(10) Patent No.: US 8,652,824 B2
(45) Date of Patent: Feb. 18, 2014

(54) RECOMBINANT POLYPEPTIDE HAVING PANCREATIC LIPASE ACTIVITY AND NUCLEIC ACID CODING SEQUENCE THEREOF, AND THEIR PRODUCTION AND USE

(75) Inventor: Fang-Chueh Liu, Tainan (TW)

(73) Assignee: Livestock Research Institute Council of Agriculture, Tainan County (TW)

( * ) Notice: Subject to any disclaimer, the term of this patent is extended or adjusted under 35 U.S.C. 154(b) by 184 days.

(21) Appl. No.: 13/028,455

(22) Filed: Feb. 16, 2011

(65) Prior Publication Data

US 2012/0009324 A1 Jan. 12, 2012

(30) Foreign Application Priority Data

Jul. 8, 2010 (TW) ................................ 99122504 A

(51) Int. Cl.
*C12N 1/20* (2006.01)
*C12N 9/20* (2006.01)
*C12N 15/00* (2006.01)
*C07H 21/04* (2006.01)

(52) U.S. Cl.
USPC ..................... 435/252.3; 435/198; 435/320.1; 536/23.2

(58) Field of Classification Search
USPC ........................................................ 435/198
See application file for complete search history.

(56) References Cited

U.S. PATENT DOCUMENTS 7,722,875 B2 * 5/2010 Beall et al. ................. 424/158.1

OTHER PUBLICATIONS

Accession No. GU576971 (Mar. 17, 2010) (embedded in the Office Action).*
Accession No. D4P6H2 May 18, 2010 (embedded in the Office Action).*
De Caro, J. et al., "Porcine Pancreatic Lipase Completion of the Primary Structure", Biochimica et Biophysica Acta, vol. 671, 1981, pp. 129-138.
Liu, Fang-Chueh et al., "Production of Recombinant Porcine Colipase Secreted by Pichia Pastoris and Its Application to Improve Dietary Fat Digestion and Growth of Postweaning Piglets", American Institute of Chemical Engineers, vol. 24, 2008, pp. 1333-1341.
Liu, Fang-Chueh et al., "Application of Porcine Lipase Secreted by Pichia Pastoris to Improve Fat Digestion and Growth Performance of Postweaning Piglets", Journal of Agricultural and Food Chemistry Article, vol. 58, 2010, pp. 3322-3329.

* cited by examiner

*Primary Examiner* — Tekchand Saidha
(74) *Attorney, Agent, or Firm* — Cesari and McKenna, LLP

(57) ABSTRACT

Disclosed herein is an isolated nucleic acid molecule encoding a recombinant polypeptide that has pancreatic lipase activity. Also disclosed herein are a recombinant vector and a recombinant host cell for producing the recombinant polypeptide. The recombinant polypeptide is adapted for preparation of an animal feed that is able to facilitate utilization of fats therein by pigs (especially postweaning pigs) and to enhance growth performance of the pigs.

16 Claims, 6 Drawing Sheets

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
cacgatgctg ctaatctgga                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
tagtgattaa cacggtgtga g                                            21

<210> SEQ ID NO 3
<211> LENGTH: 1408
<212> TYPE: DNA
```

```
<213> ORGANISM: Sus scrofa
<220> FEATURE:
<221> NAME/KEY: CDS
<222> LOCATION: (5)..(1399)
<223> OTHER INFORMATION: complete coding sequence of porcine pancreatic
      lipase (pLip gene)

<400> SEQUENCE: 3
cacgatgctg ctaatctgga cactttcgct gttgctggga gcagtactag gaagcgaagt      60
ctgtttccca agacttggct gcttcagtga tgatgcccca tgggcaggaa ttgtgcaaag     120 accccctcaaa atactgcctt gggatccaaa agatgtcaac acccgcttcc tcctatacac    180
taacgagaac caagacaact atcaagaact tgttgcagat ccatcaacta tcacagattc    240
caatttcaga atggatagaa aaacacgctt tattattcat ggattcatag acaagggaga    300
agaagactgg ctgtccaata tttgcaagaa cctgtttaag gtggagagcg tgaactgcat    360
ctgtgtggac tggaaaggcg gctcccgaac tggatacaca caagcctcac agaacatccg    420
catcgtgggg gcagaagtgg cgtattttgt tgaagttctt aagtcatcat taggatattc    480
accttccaac gtccatgtca ttggccacag cctgggttct cacgctgcag gggaggcagg    540
aagaaggacc aatgggacca ttgaacgaat acacaggctg gatccagctg aaccttgctt    600
tcaaggcaca cctgaattag tccgattgga ccccagcgat gccaagtttg tggatgtgat    660
tcacacagac gctgccccca ttatccccaa cctgggggttt ggaatgagcc aagtcgtggg    720
ccacttagat ttcttttccaa atggaggaaa agaaatgcct ggttgtcaga gaacattct    780 ctctcagatt gttgacatag acgggatctg gaaggaact cgtgactttg tggcctgtaa    840
tcacttaaga agctacaagt attatgctga tagcatcctc aaccctgatg ctttgctgg    900 atttccttgt gactcttaca atgttttcac tgcaaataag tgcttcccct gtccaagtga    960
aggctgtcca cagatgggtc attatgctga cagatttcct gggaaaacaa acggagtgag   1020
ccaggtattt tatctaaata ccggtgatgc cagcaatttc gcccgttgga gatataaagt   1080
gtctgtcaca ctatcaggaa agaaggtcac aggacacata ctcgtttctt tgtttggaaa   1140
tgaaggaaac tctaggcagt atgagattta caagggtact ctccaaccag acaatactca   1200
ctccaatgaa tttgactcag atgtagaagt tggagatttg cagaaggtga aatttatttg   1260
gtacaacaat gtgatcaacc caactctacc cagagtgggg gcatccaaga tcaccgtgga   1320
aagaaacgat ggaaaagtgt atgacttctg tagccaagaa actgtgaggg aagaagttct   1380 gctcacccctc acaccgtgtt aatcacta                                     1408

<210> SEQ ID NO 4
<211> LENGTH: 465
<212> TYPE: PRT
<213> ORGANISM: Sus scrofa
<220> FEATURE:
<221> NAME/KEY: signal
<222> LOCATION: (1)..(16)
<223> OTHER INFORMATION: amino acid sequence of signal peptide
<220> FEATURE:
<221> NAME/KEY: chain
<222> LOCATION: (17)..(465)
<223> OTHER INFORMATION: amino acid sequence of mature peptide

<400> SEQUENCE: 4

Met Leu Leu Ile Trp Thr Leu Ser Leu Leu Gly Ala Val Leu Gly
  1               5                  10                  15

Ser Glu Val Cys Phe Pro Arg Leu Gly Cys Phe Ser Asp Asp Ala Pro
                 20                  25                  30

Trp Ala Gly Ile Val Gln Arg Pro Leu Lys Ile Leu Pro Trp Asp Pro
```

```
            35                  40                  45
Lys Asp Val Asn Thr Arg Phe Leu Leu Tyr Thr Asn Glu Asn Gln Asp
 50                  55                  60
Asn Tyr Gln Glu Leu Val Ala Asp Pro Ser Thr Ile Thr Asp Ser Asn
 65                  70                  75                  80
Phe Arg Met Asp Arg Lys Thr Arg Phe Ile Ile His Gly Phe Ile Asp
                 85                  90                  95
Lys Gly Glu Glu Asp Trp Leu Ser Asn Ile Cys Lys Asn Leu Phe Lys
                100                 105                 110
Val Glu Ser Val Asn Cys Ile Cys Val Asp Trp Lys Gly Gly Ser Arg
                115                 120                 125
Thr Gly Tyr Thr Gln Ala Ser Gln Asn Ile Arg Ile Val Gly Ala Glu
                130                 135                 140
Val Ala Tyr Phe Val Glu Val Leu Lys Ser Ser Leu Gly Tyr Ser Pro
145                 150                 155                 160
Ser Asn Val His Val Ile Gly His Ser Leu Gly Ser His Ala Ala Gly
                165                 170                 175
Glu Ala Gly Arg Arg Thr Asn Gly Thr Ile Glu Arg Ile Thr Gly Leu
                180                 185                 190
Asp Pro Ala Glu Pro Cys Phe Gln Gly Thr Pro Glu Leu Val Arg Leu
                195                 200                 205
Asp Pro Ser Asp Ala Lys Phe Val Asp Val Ile His Thr Asp Ala Ala
                210                 215                 220
Pro Ile Ile Pro Asn Leu Gly Phe Gly Met Ser Gln Val Val Gly His
225                 230                 235                 240
Leu Asp Phe Phe Pro Asn Gly Gly Lys Glu Met Pro Gly Cys Gln Lys
                245                 250                 255
Asn Ile Leu Ser Gln Ile Val Asp Ile Asp Gly Ile Trp Glu Gly Thr
                260                 265                 270
Arg Asp Phe Val Ala Cys Asn His Leu Arg Ser Tyr Lys Tyr Tyr Ala
                275                 280                 285
Asp Ser Ile Leu Asn Pro Asp Gly Phe Ala Gly Phe Pro Cys Asp Ser
                290                 295                 300
Tyr Asn Val Phe Thr Ala Asn Lys Cys Phe Pro Cys Pro Ser Glu Gly
305                 310                 315                 320
Cys Pro Gln Met Gly His Tyr Ala Asp Arg Phe Pro Gly Lys Thr Asn
                325                 330                 335
Gly Val Ser Gln Val Phe Tyr Leu Asn Thr Gly Asp Ala Ser Asn Phe
                340                 345                 350
Ala Arg Trp Arg Tyr Lys Val Ser Val Thr Leu Ser Gly Lys Lys Val
                355                 360                 365
Thr Gly His Ile Leu Val Ser Leu Phe Gly Asn Glu Gly Asn Ser Arg
                370                 375                 380
Gln Tyr Glu Ile Tyr Lys Gly Thr Leu Gln Pro Asp Asn Thr His Ser
385                 390                 395                 400
Asn Glu Phe Asp Ser Asp Val Glu Val Gly Asp Leu Gln Lys Val Lys
                405                 410                 415
Phe Ile Trp Tyr Asn Asn Val Ile Asn Pro Thr Leu Pro Arg Val Gly
                420                 425                 430
Ala Ser Lys Ile Thr Val Glu Arg Asn Asp Gly Lys Val Tyr Asp Phe
                435                 440                 445
Cys Ser Gln Glu Thr Val Arg Glu Glu Val Leu Leu Thr Leu Thr Pro
450                 455                 460
```

Cys
465

<210> SEQ ID NO 5
<211> LENGTH: 449
<212> TYPE: PRT
<213> ORGANISM: Sus scrofa

<400> SEQUENCE: 5

Ser Glu Val Cys Phe Pro Arg Leu Gly Cys Phe Ser Asp Asp Ala Pro
1               5                   10                  15

Trp Ala Gly Ile Val Gln Arg Pro Leu Lys Ile Leu Pro Trp Asp Pro
            20                  25                  30

Lys Asp Val Asn Thr Arg Phe Leu Leu Tyr Thr Asn Glu Asn Gln Asp
        35                  40                  45

Asn Tyr Gln Glu Leu Val Ala Asp Pro Ser Thr Ile Thr Asp Ser Asn
    50                  55                  60

Phe Arg Met Asp Arg Lys Thr Arg Phe Ile Ile His Gly Phe Ile Asp
65                  70                  75                  80

Lys Gly Glu Glu Asp Trp Leu Ser Asn Ile Cys Lys Asn Leu Phe Lys
                85                  90                  95

Val Glu Ser Val Asn Cys Ile Cys Val Asp Trp Lys Gly Gly Ser Arg
            100                 105                 110

Thr Gly Tyr Thr Gln Ala Ser Gln Asn Ile Arg Ile Val Gly Ala Glu
        115                 120                 125

Val Ala Tyr Phe Val Glu Val Leu Lys Ser Ser Leu Gly Tyr Ser Pro
    130                 135                 140

Ser Asn Val His Val Ile Gly His Ser Leu Gly Ser His Ala Ala Gly
145                 150                 155                 160

Glu Ala Gly Arg Arg Thr Asn Gly Thr Ile Glu Arg Ile Thr Gly Leu
                165                 170                 175

Asp Pro Ala Glu Pro Cys Phe Gln Gly Thr Pro Glu Leu Val Arg Leu
            180                 185                 190

Asp Pro Ser Asp Ala Lys Phe Val Asp Val Ile His Thr Asp Ala Ala
        195                 200                 205

Pro Ile Ile Pro Asn Leu Gly Phe Gly Met Ser Gln Val Val Gly His
    210                 215                 220

Leu Asp Phe Phe Pro Asn Gly Gly Lys Glu Met Pro Gly Cys Gln Lys
225                 230                 235                 240

Asn Ile Leu Ser Gln Ile Val Asp Ile Asp Gly Ile Trp Glu Gly Thr
                245                 250                 255

Arg Asp Phe Val Ala Cys Asn His Leu Arg Ser Tyr Lys Tyr Tyr Ala
            260                 265                 270

Asp Ser Ile Leu Asn Pro Asp Gly Phe Ala Gly Phe Pro Cys Asp Ser
        275                 280                 285

Tyr Asn Val Phe Thr Ala Asn Lys Cys Phe Pro Cys Pro Ser Glu Gly
    290                 295                 300

Cys Pro Gln Met Gly His Tyr Ala Asp Arg Phe Pro Gly Lys Thr Asn
305                 310                 315                 320

Gly Val Ser Gln Val Phe Tyr Leu Asn Thr Gly Asp Ala Ser Asn Phe
                325                 330                 335

Ala Arg Trp Arg Tyr Lys Val Ser Val Thr Leu Ser Gly Lys Lys Val
            340                 345                 350

Thr Gly His Ile Leu Val Ser Leu Phe Gly Asn Glu Gly Asn Ser Arg
        355                 360                 365

```
Gln Tyr Glu Ile Tyr Lys Gly Thr Leu Gln Pro Asp Asn Thr His Ser
        370                 375                 380

Asn Glu Phe Asp Ser Asp Val Glu Val Gly Asp Leu Gln Lys Val Lys
385                 390                 395                 400

Phe Ile Trp Tyr Asn Asn Val Ile Asn Pro Thr Leu Pro Arg Val Gly
                405                 410                 415

Ala Ser Lys Ile Thr Val Glu Arg Asn Asp Gly Lys Val Tyr Asp Phe
            420                 425                 430

Cys Ser Gln Glu Thr Val Arg Glu Glu Val Leu Leu Thr Leu Thr Pro
        435                 440                 445

Cys

<210> SEQ ID NO 6
<211> LENGTH: 1347
<212> TYPE: DNA
<213> ORGANISM: Sus scrofa

<400> SEQUENCE: 6
agcgaagtct gtttcccaag acttggctgc ttcagtgatg atgccccatg ggcaggaatt      60
gtgcaaagac ccctcaaaat actgccttgg gatccaaaag atgtcaacac ccgcttcctc     120
ctatacacta acgagaacca agacaactat caagaacttg ttgcagatcc atcaactatc     180
acagattcca atttcagaat ggatagaaaa cacgcttta ttattcatgg attcatagac      240
aagggagaag aagactggct gtccaatatt tgcaagaacc tgtttaaggt ggagagcgtg     300
aactgcatct gtgtggactg aaaggcggc tcccgaactg gatacacaca gcctcacag      360
aacatccgca tcgtggggc agaagtggcg tattttgttg aagttcttaa gtcatcatta     420
ggatattcac cttccaacgt ccatgtcatt ggccacagcc tgggttctca cgctgcaggg     480
gaggcaggaa gaaggaccaa tgggaccatt gaacgaatca cagggctgga tccagctgaa     540
ccttgctttc aaggcacacc tgaattagtc cgattggacc ccagcgatgc caagtttgtg     600
gatgtgattc acacagacgc tgcccccatt atccccaacc tgggggtttgg aatgagccaa     660
gtcgtgggcc acttagattt cttttccaaat ggaggaaaag aaatgcctgg ttgtcagaag     720
aacattctct ctcagattgt tgacatagac gggatctggg aaggaactcg tgactttgtg     780
gcctgtaatc acttaagaag ctacaagtat tatgctgata gcatcctcaa ccctgatggc     840
tttgctggat tccttgtga ctcttacaat gttttcactg caaataagtg cttcccctgt     900
ccaagtgaag gctgtccaca gatgggtcat tatgctgaca gatttcctgg gaaaacaaac     960
ggagtgagcc aggtattta tctaaatacc ggtgatgcca gcaatttcgc ccgttggaga    1020
tataaagtgt ctgtcacact atcaggaaag aaggtcacag gacacatact cgtttctttg    1080
tttggaaatg aaggaaactc taggcagtat gagatttaca agggtactct ccaaccagac    1140
aatactcact ccaatgaatt tgactcagat gtagaagttg gagatttgca gaaggtgaaa    1200
tttatttggt acaacaatgt gatcaaccca actctaccca gagtgggggc atccaagatc    1260
accgtggaaa gaaacgatgg aaaagtgtat gacttctgta gccaagaaac tgtgagggaa    1320
gaagttctgc tcaccctcac accgtgt                                         1347

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
```

```
gaattcggaa gcgaagtctg tttc                                              24

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
ttctagacac ggtgtgaggg tga                                               23

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
gtccctattt caatcaattg aa                                                22

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gcaaatggca ttctgacatc c                                                 21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
agatggccga ccaatgtgac g                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
tgttccaggg tggtatgcgt g                                                 21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ttattcgcag catcctccgc                                                   20
```

RECOMBINANT POLYPEPTIDE HAVING PANCREATIC LIPASE ACTIVITY AND NUCLEIC ACID CODING SEQUENCE THEREOF, AND THEIR PRODUCTION AND USE

CROSS-REFERENCE TO RELATED APPLICATION

This application claims priority of Taiwanese Application No. 099122504, filed on Jul. 8, 2010.

BACKGROUND OF THE INVENTION

1. Field of the Invention

This invention relates to an isolated nucleic acid sequence having a nucleotide sequence that encodes a recombinant polypeptide having pancreatic lipase activity. This invention also relates to a recombinant vector and a recombinant host cell for producing the recombinant polypeptide. The recombinant polypeptide is adapted for preparation of an animal feed that is able to facilitate utilization of fats therein regarding pigs (especially postweaning piglets) and to enhance growth performance of the pigs.

2. Description of the Related Art

Generally, growth period of a pig can be divided into the following four phases: lactation phase, nursery phase, grower phase, and finisher phase. During the lactation phase, a newborn piglet (a body weight of about 1.5 kg) obtains energy from sow's milk. During the nursery phase, the weaned piglet (a body weight of about 6~7 kg) grows and becomes a 5~2-week-old nursery pig (a body weight of about 7~30 kg). The nursery pig grows and becomes a 13~20-week-old grower pig (a body weight of about 30~60 kg) during the grower phase. The grower pig grows and becomes a 21~30-week-old finisher pig (a body weight of about 60~110 kg) during the finisher phase.

After entering the nursery phase, due to change of feed form, gastrointestinal tract development of the piglet is adversely influenced, e.g., insufficient secretion of digestive enzyme, reduction in absorption ability caused by change of intestinal villus structure, insufficient secretion of gastric acid, etc. Accordingly, feed intake and digestibility of the postweaning piglet are further decreased such that the postweaning piglet may undergo growth stasis (also known as postweaning lag).

In order to prevent energy deficiency phenomenon induced by postweaning lag, a method of maintaining caloric intake of postweaning piglets by adding various fat sources to a feed for the postweaning piglets is widely developed. A report has indicated that utilization of fats in a feed regarding postweaning piglets varies with the type of fats and the fat content. In contrast with animal fats, plant fats have a higher level of middle chain triglyceride (MCT) and unsaturated fatty acids such that the plant fats can be more easily digested and absorbed by postweaning piglets (K. R. Cera et al. (1988), *J. Anim. Sci.*, 66:1430-1437; K. R. Cera et al. (1990), *J. Anim. Sci.*, 68:2756-2765). However, in the second week after weaning, fat utilization of piglets is reduced on account of gradual decrease in pancreatic lipase activity, and the piglets are hence not capable of acquiring sufficient energy to maintain growth performance thereof (C. A. Flores et al. (1988), *J. Pediatr. Gastroenterol. Nutr.*, 7:914-921; M. S. Jensen et al. (1997), *J. Anim. Sci.*, 75:437-445). Accordingly, how to facilitate utilization of fats in a feed with respect to postweaning piglets is required to be investigated for the pig-farming industry and animal feed manufacturers so that the postweaning piglets are able to sufficiently obtain essential energy for growth.

Pancreatic lipase is an enzyme that is secreted by the pancreas, and is able to hydrolyze fat molecules. In the pancreas, newly formed pancreatic lipase is an inactive proenzyme that is composed of a signal peptide and a mature peptide, and that has 465 amino acid residues. Amino acid residues 1-16 constitute the signal peptide, and amino acid residues 17-465 constitute the mature peptide. When the signal peptide is subjected to cleavage processing by virtue of pancreatic protease, the inactive pancreatic lipase is converted to the active pancreatic lipase having fat-hydrolysis activity.

Due to rapid development of biotechnology, amino acid sequences of pancreatic lipases of numerous species and complete coding sequences thereof have been investigated and are available in the database at the NCBI (National Center for Biotechnology Information) website. For example, the following sequences can be found at the NCBI website: the amino acid sequence of pancreatic lipase of *Homo sapiens* (NCBI Accession No. 10835000) and the complete coding sequence thereof (NCBI Accession No. M93285); the amino acid sequence of pancreatic lipase of *Mus musculus* (NCBI Accession No. 37674236) and the complete coding sequence thereof (NCBI Accession No. BC061061); the amino acid sequence of pancreatic lipase of *Rattus norvegicus* (NCBI Accession No. 6981376) and the complete coding sequence thereof (NCBI Accession No. 6981375); the amino acid sequence of pancreatic lipase of *Equus caballus* (NCBI Accession No. 255653018) and the complete coding sequence thereof (NCBI Accession No. 255653017); and the amino acid sequence of pancreatic lipase of *Canis familiaris* (NCBI Accession No. 73998882) and the complete coding sequence thereof (NCBI Accession No. 50919159).

J. De Caro et al. isolated and purified porcine pancreatic lipase from porcine pancreatic tissues, subsequently conducted fragmentation on the porcine pancreatic lipase using CNBr to obtain peptide fragments, and acquired the amino acid sequence of the porcine pancreatic lipase by virtue of automated sequence analysis [J. De Caro et al. (1981), *Biochim. Biophys. Acta*, 671:129-138]. Even though the amino acid sequence of the porcine pancreatic lipase has been studied thoroughly, the applicants are unaware of any literature or prior art patent that has disclosed a complete coding sequence of the porcine pancreatic lipase.

In order to facilitate utilization of fats in a feed with respect to postweaning piglets, researchers in the related fields normally use pancreatic lipase directly obtained from the pancreas or various substances able to enhance pancreatic lipase activity as feed additives, and add the same into a feed for postweaning piglets so that activity of the pancreatic lipase in the postweaning piglets can be strengthened. For instance, U.S. Pat. No. 7,153,504 B2 has disclosed a stabilized pancreas product containing an emulsification of whole pancreas, which is blended with soy hulls. The emulsification of whole pancreas contains one or more pancreatic enzymes in zymogen form. The experimental results have indicated that the stabilized pancreas product can be used as an animal feed additive so as to facilitate utilization of nutrients with respect to an animal when the animal encounters a production change (e.g., a change in a feed or environment).

CN 101366451A discloses a feed additive for improving a fat digestion utilization ratio and a method for preparing the same. The feed additive contains the following components: 0-35 parts by weight of bile acid, 0-15 parts by weight of taurine, and 20-80 parts by weight of defatted rice bran. The experimental results reveal that: addition of a proper amount of bile acid and taurine into a feed is able to enhance activity of pancreatic lipase, to greatly improve the fat digestion utilization ratio, and to strengthen liver function, thereby lowering the incidence rate of animal fatty liver and the mortality of animals.

In an animal body, hydrolysis of fat molecules depends not only on pancreatic lipase, but also on pancreatic colipase. Therefore, adding pancreatic colipase to a feed for postweaning piglets is another possible way to enhance utilization of fats in the feed regarding the postweaning piglets. TW 200916584 discloses an isolated pancreatic colipase, and a method for enhancing growth performance of a pig using a feed additive containing the isolated pancreatic colipase. The experimental results indicate that: compared to the control group, during 4 weeks of feeding postweaning piglets with a feed containing the 5000 U/kg pancreatic colipase, the body weight of the postweaning piglets significantly increased at Days 15, 22, and 28; average daily gain (ADG) of the postweaning piglets significantly increased in the periods of Days 1-7 and Days 8-14, but is not significantly different from that of the control group in the periods of Days 15-21 and Days 22-28; and average daily feed intake (ADFI) and feed efficiency (FE) of the postweaning piglets are not significantly different from those of the control group during the overall period of the experiment.

Even though the aforementioned prior art patents can be applied to increase activity of pancreatic lipase in postweaning piglets so as to facilitate utilization of fats in a feed regarding the postweaning piglets (i.e., so as to facilitate conversion of the fats in the feed to essential needs for growth of the postweaning piglets), a long-term facilitation effect and a reduction in production cost of the feed are still in demand. Furthermore, most of conventional methods for investigating porcine pancreatic lipase employ a protein purification step to purify the porcine pancreatic lipase from frozen pancreatic tissues. However, the protein purification step is time-consuming and complicated, and the amount of the thus obtained porcine pancreatic lipase is insufficient. Therefore, using the porcine pancreatic lipase obtained by the aforesaid conventional methods as a feed additive for postweaning piglets may give rise to a high production cost. In addition, a production cost of the artificial porcine pancreatic lipase produced using the conventional peptide synthesis technology may be higher than that of the porcine pancreatic lipase obtained by the aforesaid protein purification step.

In order to overcome the drawbacks of the prior art patents, genetic engineering technology may be used to clone the coding gene of porcine pancreatic lipase, thereby inducing mass production of recombinant porcine pancreatic lipase. Accordingly, the applicants attempted to clone porcine pancreatic lipase gene (pLip gene) from porcine pancreatic tissues, and to employ genetic engineering technology for rapidly and massively producing recombinant porcine pancreatic lipase. The applicants used the obtained recombinant porcine pancreatic lipase to prepare an animal feed and fed the postweaning piglets with the animal feed. The applicants subsequently found that: the postweaning piglets were able to effectively utilize fats in the animal feed as an energy source, and growth performance of the postweaning piglets was enhanced accordingly.

SUMMARY OF THE INVENTION

Therefore, according to a first aspect, this invention provides an isolated nucleic acid sequence having a nucleotide sequence encoding a polypeptide that has an amino acid sequence selected from the group consisting of:

(i) an amino acid sequence as shown in SEQ ID NO:4; and
(ii) an amino acid sequence as shown in SEQ ID NO:5.

According to a second aspect, this invention provides a recombinant vector having the isolated nucleic acid sequence as described in the first aspect and a promoter sequence that is operatively connected upstream of the isolated nucleic acid sequence.

According to a third aspect, this invention provides a recombinant host cell produced from transformation of a host cell with the recombinant vector as described in the second aspect.

According to a fourth aspect, this invention provides a recombinant polypeptide having pancreatic lipase activity. The recombinant polypeptide has an amino acid sequence as shown in SEQ ID NO:5.

According to a fifth aspect, this invention provides an animal feed comprising the recombinant polypeptide as described in the fourth aspect.

BRIEF DESCRIPTION OF THE DRAWINGS

The above and other features and advantages of the present invention will become apparent in the following detailed description of the preferred embodiments with reference to the accompanying drawings, of which.

Figure 6:
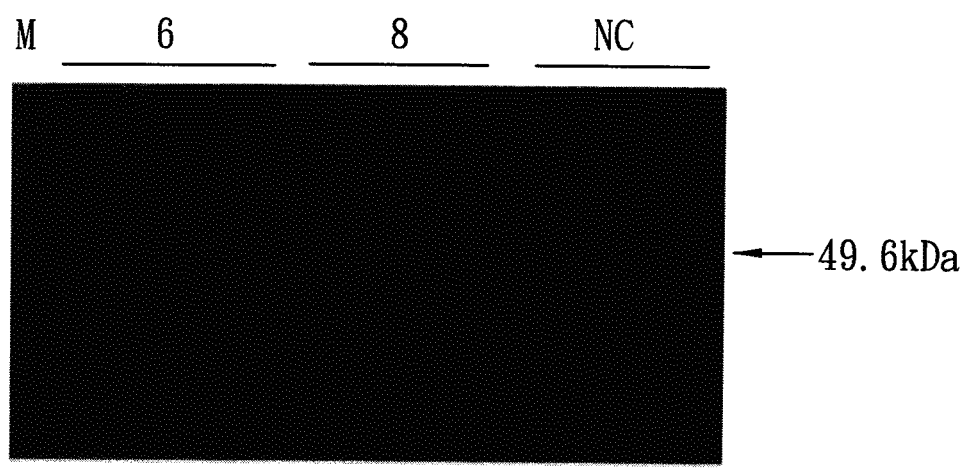
Figure 7:
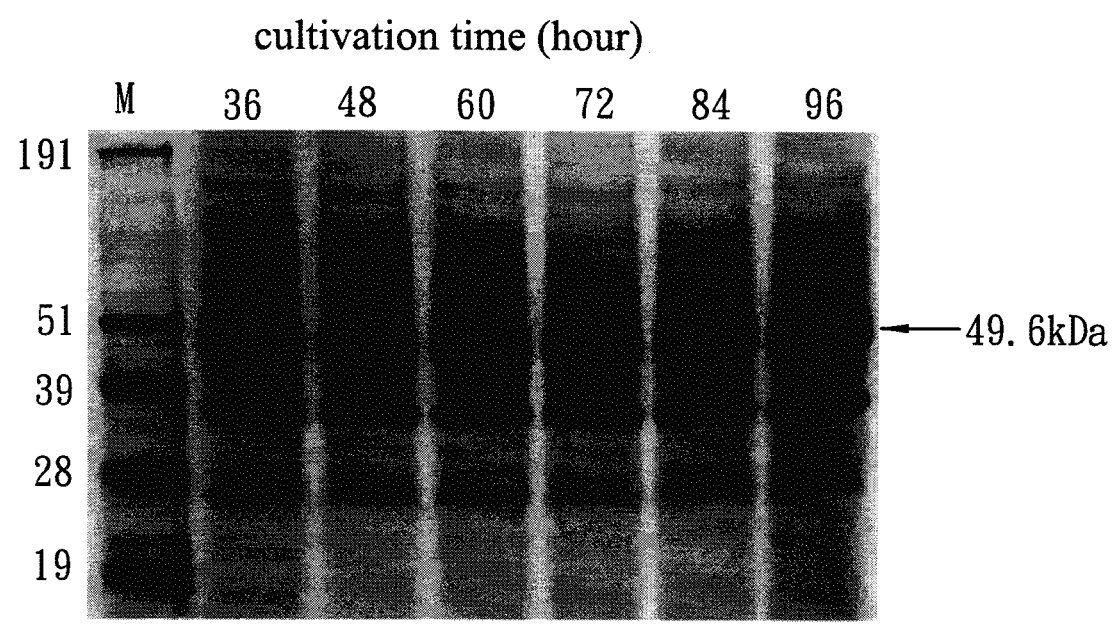

*pastoris* GS115 transformant containing pGAPZα A vector; and lanes 6 and 8 respectively show the protein samples of *Pichia pastoris* GS115 transformants 6 and 8 containing pGAPZα A-pLip recombinant vector;

FIG. 6 is a Western blot showing the immunodetection of recombinant porcine pancreatic lipase produced by *Pichia pastoris* GS115 transformants 6 and 8 using mouse anti-myc monoclonal antibody, in which lane M shows the immunodetection result of the protein ladder markers; lanes NC (negative control) show the immunodetection result of the protein sample of the *Pichia pastoris* GS115 transformant containing pGAPZα A vector; and lanes 6 and 8 respectively show the immunodetection results of the protein samples of *Pichia pastoris* GS115 transformants 6 and 8 containing pGAPZα A-pLip recombinant vector; and FIG. 7 is a protein electrophoretogram showing the expression level of recombinant porcine pancreatic lipase in the filtrate formed from the culture obtained at the respective cultivation time (36 hrs, 48 hrs, 60 hrs, 72 hrs, 84 hrs, or 96 hrs) of *Pichia pastoris* GS115 transformant 6, in which lane M shows the protein ladder markers.

DETAILED DESCRIPTION OF THE PREFERRED EMBODIMENTS

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

The terms "polypeptide", "peptide", and "protein" as used herein can be interchangeably used, and refer to a polymer formed of amino acid residues, wherein one or more amino acid residues are naturally occurring amino acids or artificial chemical mimics. The term "recombinant polypeptide" or "recombinant protein" as used herein refers to polypeptides or proteins produced by recombinant DNA techniques, i.e., produced from cells transformed by an exogenous DNA construct encoding the desired polypeptide or the desired protein.

As used herein, an amino acid can be represented by the full name thereof, by the three-letter symbol corresponding thereto, or by the one-letter symbol corresponding thereto, as well-known in the art. In addition, the proteins are represented in accordance with the conventional way of describing peptides, that is, with the N-terminus (amino terminus) on the left side and the C-terminus (carboxyl terminus) on the right side.

A "DNA coding sequence" is a double-stranded DNA sequence that is transcribed into an RNA (further translated into a polypeptide) in vivo under the control of appropriate regulatory sequences. The boundaries of the DNA coding sequence are determined by a start codon at the 5' (amino) terminus and a stop codon at the 3' (carboxyl) terminus. A coding sequence may include, but is not limited to, cDNA from eukaryotic mRNA, genomic DNA sequences from eukaryotic (e.g., mammalian) DNA, and even synthetic DNA sequences. "cDNA" is defined as copy DNA or complementary DNA, and is a product of a reverse transcription reaction from an mRNA transcript.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "gene", "cDNA", "mRNA", "oligo-nucleotide", and "polynucleotide" in use.

As used herein, the terms "nucleic acid fragment" and "DNA fragment" can be interchangeably used, and refer to a DNA polymer that may be in a form of a separate segment or a component of a larger DNA construct, that may be derived from isolated DNA, or that may be chemically or enzymatically synthesized using methods well known to one of ordinary skill in the art.

The term "isolated nucleic acid sequence" as used herein refers to a polynucleotide molecule that has a limited nucleic acid sequence, and that has been isolated or purified to be adapted for use in genetically engineered protein production systems. The isolated nucleic acid sequence may be obtained from an original natural environment thereof, and includes, but is not limited to, cDNA, genomic clones, and polynucleotides or nucleic acid sequences resulting from DNA shuffling experiments or site-directed mutagenesis experiments. As used herein, the term "isolated nucleic acid sequence" can be interchangeably used with the terms "isolated polynucleotide", "isolated DNA sequence", "cloned polynucleotide", "cloned nucleic acid sequence", and "cloned DNA sequence".

Unless otherwise indicated, a nucleic acid sequence, in addition to the specific sequences described herein, also covers its complementary sequence, and the conservative analogs, related naturally occurring structural variants and/or synthetic non-naturally occurring analogs thereof, for example, homologous sequences having degenerative codon substitution, and conservative deletion, insertion, substitution, or addition. Specifically, degenerative codon substitution may be produced by, for instance, a nucleotide residue substitution at the third position of one or more selected codons in a nucleic acid sequence with other nucleotide residue(s).

The term "promoter sequence" as used herein refers to a DNA sequence, which is generally located upstream of a gene present in a DNA polymer, and which provides a site for initiation of the transcription of said gene into mRNA. Promoter sequences suitable for use in this invention may be derived from viruses, bacteriophages, prokaryotic cells or eukaryotic cells, and may be a constitutive promoter or an inducible promoter.

The term "operatively connected" as used herein means that a first sequence is disposed sufficiently close to a second sequence such that the first sequence can influence the second sequence or regions under the control of the second sequence. For instance, a promoter sequence may be operatively connected to a gene sequence, and is normally located at the 5'-terminus of the gene sequence such that the expression of the gene sequence is under the control of the promoter sequence. In addition, a regulatory sequence may be operatively connected to a promoter sequence so as to enhance the ability of the promoter sequence in promoting transcription. In such case, the regulatory sequence is generally located at the 5'-terminus of the promoter sequence.

The terms "recombinant vector" and "expression vector" as used herein can be interchangeably used, and refer to any recombinant expression system capable of expressing a selected nucleic acid sequence, in any competent host cell in vitro or in vivo, constitutively or inducibly. The recombinant vector may be an expression system in linear or circular form, and covers expression systems that remain episomal or that integrate into the host cell genome. The recombinant expression system may or may not have the ability to self-replicate, and it may drive only transient expression in a host cell.

As used herein, the term "transformation" can be used interchangeably with the term "transfection" and refers to the introduction of an exogenous nucleic acid molecule into a selected host cell. According to techniques known in the art, a nucleic acid molecule (e.g., a recombinant DNA construct or a recombinant vector) can be introduced into a selected host cell in various ways, such as calcium phosphate- or calcium chloride-mediated transfection, electroporation, microinjection, particle bombardment, liposome-mediated transfection, transfection using bacterial bacteriaphages, or other methods.

The terms "cell", "host cell", "transformed host cell", and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

After weaning, piglets are incapable of effectively utilizing fats in feeds to acquire energy required for growth due to reduction of pancreatic lipase activity in the piglets. While numerous methods of enhancing pancreatic lipase activity in postweaning piglets have been widely developed, a new method of rapidly, stably, and massively producing porcine pancreatic lipase is still in great demand in the pig-breeding industry.

As far as the applicants know, none of literatures or prior art patents has hitherto disclosed identification of the gene of porcine pancreatic lipase. Therefore, the applicants attempted to clone a complete coding sequence of pancreatic lipase from pigs so as to massively and stably produce pancreatic lipase.

In this invention, the applicants designed a primer pair, pLip-F (SEQ ID NO: 1) and pLip-R (SEQ ID NO:2), based on the complete coding sequence of *Mus musculus* pancreatic lipase mRNA (NCBI Accession No. BC061061) and the complete coding sequence of human pancreatic lipase mRNA (NCBI Accession No. M93285), and used cDNA produced from pancreatic cell mRNA of LYD three-breed commercial hog (available from Animal Industry Division, Livestock Research Institute, Council of Agriculture, Taiwan) as templates so as to conduct polymerase chain reaction (PCR), thereby obtaining a PCR product (1408 bps) having a nucleotide sequence as shown in SEQ ID NO: 3. The PCR product was analyzed using Blastx program at the NCBI website and was hence deduced to have an amino acid sequence as shown in SEQ ID NO:4. Afterward, the aforesaid deduced amino acid sequence was subjected to comparison analysis by virtue of protein database at the NCBI website, and the following was found: the deduced amino acid sequence has 98% sequence identity to the amino acid sequence of pancreatic lipase of *Sus scrofa*. The applicants accordingly presumed that: the nucleotide sequence (SEQ ID NO:3) of the aforementioned PCR product indeed is able to encode porcine pancreatic lipase; nucleotide residues 1-4 and nucleotide residues 1403-1408 constitute non-coding sequences; nucleotide residues 5-1399 constitute the complete coding sequence (named pLip gene) of porcine pancreatic lipase; and a stop codon is at nucleotide positions 1400-1402. Porcine pancreatic lipase (SEQ ID NO:4) encoded by pLip gene has 465 amino acids. Specifically, regarding porcine pancreatic lipase, the $1^{st}$-$16^{th}$ amino acid residues from the N-terminus constitute a signal peptide (encoded by nucleotide residues 5-52 of the aforementioned PCR products), and the $17^{th}$-$465^{th}$ amino acid residues from the N-terminus constitute a mature peptide (SEQ ID NO:5, encoded by nucleotide residues 53-1399 of the aforementioned PCR products).

Porcine pancreatic lipase encoded by pLip gene only has activity after the signal peptide is cleaved using trypsin. In order to more rapidly obtain a large amount of porcine pancreatic lipase having activity, the applicants attempted to insert a nucleic acid sequence (SEQ ID NO:6) encoding the aforesaid mature peptide into a vector. The resultant recombinant vector was used to transform a host cell so as to form a recombinant host cell. It is found from the experimental results that the recombinant host cell is able to produce massive recombinant polypeptides having the amino acid sequence as shown in SEQ ID NO:5. The recombinant polypeptides are proven to have stable pancreatic lipase activity by virtue of analysis of enzyme activity.

Accordingly, this invention provides an isolated nucleic acid sequence having a nucleotide sequence encoding a polypeptide that has an amino acid sequence selected from the group consisting of:
(i) an amino acid sequence as shown in SEQ ID NO:4; and
(ii) an amino acid sequence as shown in SEQ ID NO:5.

In a preferred embodiment of this invention, the nucleotide sequence of the isolated nucleic acid sequence is a nucleotide sequence as shown in SEQ ID NO:3. In another preferred embodiment of this invention, the nucleotide sequence of the isolated nucleic acid sequence is a nucleotide sequence as shown in SEQ ID NO: 6. Specifically, the nucleotide sequence as shown in SEQ ID NO:3 is able to encode the polypeptide having the amino acid sequence as shown in SEQ ID NO:4, and the nucleotide sequence as shown in SEQ ID NO:6 is able to encode the polypeptide having the amino acid sequence as shown in SEQ ID NO:5.

The isolated nucleic acid sequence according to this invention can be utilized to construct various recombinant vectors for transforming a variety of host cells.

Therefore, this invention also provides a recombinant vector that has a nucleotide sequence as shown in SEQ ID NO:3 or SEQ ID NO:6, and a promoter sequence operatively connected upstream of the aforementioned nucleotide sequence. In a preferred embodiment of this invention, the recombinant vector has the nucleotide sequence as shown in SEQ ID NO:6.

The recombinant vector according to this invention can be prepared using a standard technique known to one of ordinary skill in the art. Vectors suitable for use in this invention include those commonly used in genetic engineering technology, such as bacteriophages, plasmids, cosmids, viruses, or retroviruses. Preferably, the vector is selected from the group consisting of: pGAPZα A, pGAPZα B, and pGAPZα C.

The promoter sequence of the recombinant vector according to this invention has a promoter. The promoter suitable for use in this invention includes, but is not limited to, $P_{GAP}$, $P_{TEF1}$, and $P_{EM7}$. In a preferred embodiment of this invention, the promoter is $P_{GAP}$.

Vectors suitable for use in this invention may include other expression control elements, such as a transcription starting site, a transcription termination site, a ribosome binding site, a RNA splicing site, a polyadenylation site, a translation termination site, etc. Vectors suitable for use in this invention may further include additional regulatory elements, such as transcription/translation enhancer sequences, Shine-Dalgarno (SD) sequences, regulatory sequences, and at least a marker gene (e.g., antibiotic-resistance gene) or reporter gene allowing for the screening of the vectors under suitable conditions. Marker genes suitable for use in this invention include, for instance, dihydrofolate reductase gene and resistance genes for G418, neomycin, or Zeocin useful in eukaryotic cell cultures, and resistance genes for ampicillin, streptomycin, tetracycline, or kanamycin useful in *E. coli* and other bacterial cultures.

In addition, vectors suitable for use in this invention may further include a secretion signal coding sequence that is located at 5' end of the nucleic acid sequence according to this invention so that a secretion signal peptide is expressed and is located at N-terminus of the expressed recombinant polypeptide. For instance, when hosts are bacteria belonging to *Escherichia* sp., PhoA signal sequence, OmpT signal sequence, OmpA signal sequence, etc. can be used; when hosts are bacteria belonging to *Bacillus* sp., α-amylase signal sequence, subtilisin signal sequence, etc. can be utilized; when hosts are yeasts, MFα signal sequence, SUC2 signal sequence, α-factor signal sequence, etc. can be used; and when hosts are animal cells, insulin signal sequence, α-interferon signal sequence, antibody molecule signal sequences, etc. can be utilized. In a preferred embodiment of this invention, the secretion signal coding sequence is an α-factor signal sequence. The aforementioned sequences are well known to those skilled in the art.

The recombinant vector according to this invention can be used to transform or transfect a desired host cell. Consequently, this invention provides a recombinant host cell that is produced from transformation of a host cell with the aforesaid recombinant vector.

In a preferred embodiment of this invention, the recombinant host cell is produced from transformation of a host cell with the recombinant vector carrying the isolated nucleic acid sequence that has the nucleotide sequence encoding the polypeptide of the amino acid sequence as shown in SEQ ID NO:5. In a more preferred embodiment of this invention, the recombinant host cell is produced from transformation of a host cell with the recombinant vector carrying the isolated nucleic acid sequence having the nucleotide sequence as shown in SEQ ID NO:6.

Host cells suitable for use in this invention may be prokaryotic cells or eukaryotic cells, and may be non-transformed/transfected cells or transformed/transfected cells that have at least one recombinant nucleic acid sequence different from the recombinant vector according to this invention. Preferably, host cells are selected from the group consisting of yeast cells, *Escherichia coli* cells, insect cells, and mammalian cells. In a preferred embodiment of this invention, the host cells used for production of the recombinant host cells are yeast cells. In a more preferred embodiment of this invention, the host cells used for production of the recombinant host cells are *Pichia pastoris* cells.

Suitable culture media and culture conditions for host cells suitable for carrying out DNA recombination techniques are well known in the field of biotechnology. For instance, host cells may be cultured in a fermentation bioreactor, a shaking flask, a test tube, a microtiter plate, or a petri dish, and cultivation of the host cells may be conducted under conditions suitable for growth of said cells.

The recombinant protein formed according to this invention may be a single protein or a fusion protein depending on the selected vector system and the insertion position of the isolated nucleic acid sequence according to this invention at the selected vector. For example, when the isolated nucleic acid sequence according to this invention is inserted into a vector that has a gene sequence encoding another protein (e.g., a reporter gene), and the insertion position results in connection of the isolated nucleic acid sequence according to this invention with the aforesaid gene sequence or partial overlapping of the end portion of the isolated nucleic acid sequence according to this invention with the aforesaid gene sequence, a recombinant fusion protein may be expressed. A spacer can be inserted when necessary so as to prevent the activity of the recombinant fusion protein from being adversely affected. This technique is well known to one of ordinary skill in the art.

Depending on the vector and host cell system used, the recombinant polypeptide (protein) produced according to this invention may either remain within the recombinant host cell, may be secreted into the culture medium, may be secreted into a periplasmic space, or may be retained on an outer surface of a cell membrane. The recombinant polypeptide produced by the method of this invention can be purified using a variety of standard protein purification techniques.

Basically, after the transformed host cells are cultured for a sufficient amount of time, the transformed host cells are collected by virtue of the conventional method and are subsequently suspended in a suitable buffer solution. The transformed host cells are broken using ultrasonic wave, lysozyme, and/or freeze-dissolution method. A protein crude extract is formed via centrifugal separation and/or filtration. The buffer solution may contain protein denaturants (e.g., urea, guanidine hydrochloride, etc.) and surfactants (e.g., Triton X-100).

In the case that the recombinant polypeptide is secreted into the culture medium, after cultivation, the cells are separated from the culture medium using a suitable method. The proteins in the supernatant can be purified by conventional protein isolation and purification techniques including, but not limited to, salting out, solvent precipitation, dialysis, ultrafiltration, gel filtration, centrifugal filtration, sodium dodecyl sulfate-polyacrylamide gel electrophoresis (SDS-PAGE), isoelectric focusing electrophoresis, reverse phase chromatography, anion exchange chromatography, affinity chromatography, chromatofocusing, etc.

In a preferred embodiment of this invention, the recombinant polypeptide has an α-factor signal peptide at the N-terminus thereof. Therefore, the recombinant polypeptide can be hence secreted into the culture medium from the yeast host cell, and can be purified and recovered using centrifugal filtration.

The recombinant polypeptide produced according to this invention is preferably recovered in "substantially pure" form. As used herein, the term "substantially pure" refers to a purity of a purified polypeptide which allows for the effective use of said purified polypeptide as a commercial product.

According to this invention, *Pichia pastoris* GS115 transformant, which is produced from transformation of *Pichia pastoris* GS115 cell with the recombinant vector carrying the isolated nucleic acid sequence having the nucleotide sequence as shown in SEQ ID NO:6, is able to steadily generate the recombinant polypeptide that has the amino acid sequence as shown in SEQ ID NO:5 and pancreatic lipase activity. The applicants further added the aforesaid recombinant polypeptide having pancreatic lipase activity to an animal feed and fed postweaning piglets with the animal feed. It is verified from the experimental results that: the recombinant polypeptide according to this invention is capable of effectively facilitating utilization and digestion of fats in the animal feed with respect to the postweaning piglets, thereby further enhancing growth performance of the postweaning piglets.

In view of the foregoing favorable bioactivity, the recombinant polypeptide of this invention is expected to be capable of serving as a feed additive that can be used to facilitate utilization of fats in an animal feed with respect to an animal. Accordingly, this invention provides an animal feed containing the aforementioned recombinant polypeptide.

The term "growth performance" as used herein refers to growth rate or feed efficiency.

The term "feed" as used herein refers to any suitable or desired compounds, preparations, mixtures, or compositions to be subjected to intake by an animal.

The recombinant polypeptide of this invention can be added to an animal feed using a standard technique well known to one of ordinary skill in the art. For instance, the recombinant polypeptide may be directly added to an animal feed, or may be utilized to prepare an intermediate composition (e.g., a feed additive or a premix) suitable to be subsequently added to an animal feed. In a preferred embodiment of this invention, the animal feed of this invention is prepared by mixing the dried recombinant polypeptide product formed according to this invention and an animal basal diet together.

The animal feed according to this invention may be orally administrable, and can be formulated into a form, including, but not limited to, liquid form, solid form (such as powder form, granular form, particulate form, or a compressed tablet), gel form, and slurry form, by virtue of a technique well known to one of ordinary skill in the art. In a preferred embodiment of this invention, the animal feed is in solid form. In a more preferred embodiment of this invention, the animal feed is in powder form.

According to this invention, the amount of the recombinant polypeptide is 0.1%-0.5% (w/w) based on the total weight of the animal feed. In a preferred embodiment of this invention, the amount of the recombinant polypeptide is 0.2%-0.4% (w/w) based on the total weight of the animal feed.

The animal feed according to this invention may further contain a dietary additive or a health ingredient. The dietary additive and the health ingredient are widely used in preparation of feeds and include, but are not limited to, vitamins, microminerals, amylase, protease, and phytase.

According to this invention, the animal feed may be administered to an animal needing pancreatic lipase to hydrolyze fats, including, but not limited to, cattle, a deer, a pig, a goat, a sheep, a chicken, or a duck. In a preferred embodiment of this invention, the animal feed is administered to pigs, in particular, postweaning piglets.

According to this invention, the amount and the frequency of administration of the animal feed may vary depending on the following factors: the weight, the age, the physical condition, and the response of the animal to be fed. Generally speaking, the daily administration amount of the animal feed according to this invention may be 30 to 50 g per kilogram of the body weight, and may be given as a single administration or several administrations.

This invention will be further described by way of the following examples. However, it should be understood that the following examples are solely intended for the purpose of illustration and should not be construed as limiting the invention in practice.

EXAMPLES

General Experimental Materials and Methods

1. The DNA cloning techniques and the following experimental methods, e.g., DNA cleavage reaction employing restriction enzymes, polymerase chain reaction (PCR), DNA ligation with T4 DNA ligase, agarose gel electrophoresis, Western blotting, plasmid transformation, etc., were conducted using the techniques described in the following textbook well known in the art, Sambrook J, Russell DW (2001) Molecular Cloning: a Laboratory Manual, 3rd ed. Cold Spring Harbor Laboratory Press, New York, as reference.
2. The restriction enzymes used in the following examples, EcoRI, XbaI, and BglII, were purchased from New England Biolabs.
3. The PCR primers used in the following examples were synthesized by Invitrogen.
4. The following experimental materials were purchased from Invitrogen: *Pichia pastoris* GS115, YPD broth (containing 10 g/L yeast extract, 20 g/L Bacto peptone, and 20 g/L dextrose), TRIzol™ reagent, FastTrack MAG mRNA isolation kit, SuperScript™ III First-Strand Synthesis System (Cat. No. 18080-051), random hexamer primer, NuPAGE® Novex Bis-Tris Gels, pGAPZα A vector, Zeocin, Xcell SureLock™ Mini-cell, NuPAGE® MES SDS running buffer, SimplyBlue™ Safestain, T4 DNA ligase (Cat. No. 15224-041), and mouse anti-myc monoclonal antibody (Cat. No. R950-25).
5. Goat anti-mouse IgG-HRP antibody (Cat. No. NEF822) was purchased from PerkinElmer.
6. The following experimental materials were purchased from Pointe Scientific Inc.: PRO200 homogenizer, Triglyceride-GPO Reagent Set, and Liquid Urea Nitrogen (BUN) Reagent Set.
7. pGEM T-Easy vector was purchased from Promega (Madison, Wis.).
8. Gel Advance™ gel extraction system was purchased from Viogene.
9. High Pure PCR Template Preparation Kit (Cat. No. 11796828001) was purchased from Roche Applied Science.
10. RNeasy Mini Kit was purchased from Qiagen (Valencia, Calif.).
11. Landrace×Yorkshire×Duroc three-breed commercial hogs (LYD three-breed commercial hog) and LYD three-breed piglets were obtained from Animal Industry Division, Livestock Research Institute, Council of Agriculture, Taiwan.

Example 1

Cloning of Porcine Pancreatic Lipase Gene (pLip Gene)

A. Extraction of Poly($A^+$) mRNA from Porcine Pancreatic Cells

A 12-week old LYD three-breed commercial hog was anesthetized by intramuscularly injecting ketamine with a dose of 10 mg/Kg, followed by conducting carotid artery bleeding so as to sacrifice the LYD three-breed commercial hog. The pancreas was taken out and was ground using PRO200 homogenizer. Subsequently, 1 g of ground pancreatic tissues was acquired and was subjected to total RNA extraction using TRIzol™ reagent according to the manufacturer's instructions. 300 μg of the thus obtained total RNAs was subjected to isolation of poly(A+) mRNA using Fast-Track MAG mRNA isolation kit, thereby obtaining poly(A+) mRNA of porcine pancreatic cells.

B. Reverse Transcription-Polymerase Chain Reaction (RT-PCR)

First-strand cDNA was synthesized using SuperScript™ III First-Strand Synthesis System according to the manufacturer's instruction. Specifically, 50 ng of poly(A+) mRNA obtained in the preceding section A was mixed with 1 μL of oligo (dT) primer and 1 μL of 10 nm dNTP, followed by adding diethylpyrocarbonate (DEPC)-water so as to reach a final volume of 10 μL and mixing uniformly. Afterward, the resultant mixture was placed in a PCR machine (GeneAmp® PCR System 2700, Applied Biosystem) and was heated at 65° C. for 5 minutes. The mixture was then placed on ice for 1 minute. 10 μL of cDNA Synthesis Mix [containing 1 μL of SuperScript™ III reverse transcriptase (200 U/μL), 2 μL of 10× reverse transcriptase buffer solution, 4 μL of 25 mM MgCl$_2$, 2 μL of 0.1 M DTT, and 1 μL of RNaseOUT™ (40 U/μL)] was added. The newly formed mixture was placed in the PCR machine, and was subjected to reverse transcription at 50° C. for 50 minutes, followed by heating at 85° C. for 5 minutes so as to terminate the enzymatic reaction. First-strand cDNA was therefore acquired.

The acquired first-strand cDNA served as templates, and the primer pair, pLip-F and pLip-R, was designed based on the complete coding sequence of *Mus musculus* pancreatic lipase mRNA (NCBI Accession No. BC061061) and the complete coding sequence of human pancreatic lipase mRNA (NCBI Accession No. M93285) so as to be used in a PCR experiment having reaction conditions as shown in Table 1. The nucleotide sequences of pLip-F primer and pLip-R primer are shown below.

```
pLip-F primer
5'-cacgatgctgctaatctgga-3'      (SEQ ID NO: 1)

pLip-R primer
5'-tagtgattaacacggtgtgag-3'     (SEQ ID NO: 2)
```

TABLE 1

Reaction conditions used in PCR experiment

| Content | Volume (μL) |
|---|---|
| First-strand cDNA (0.2 μg/μL) | 1 |
| pLip-F primer (0.5 μM) | 1 |
| pLip-R primer (0.5 μM) | 1 |
| dNTPs (10 mM) | 1 |
| Taq DNA polymerase buffer (10X) | 5 |
| Platinum ® Taq DNA polymerase High Fidelity (5 U/μL) | 0.2 |
| MgSO$_4$ (50 mM) | 2 |
| deionized water | 38.8 |

Operating conditions: denaturation at 94° C. for 2 minutes; followed by 30 cycles of the following reactions: denaturation at 94° C. for 30 seconds, primer annealing at 58° C. for 30 seconds, and elongation/extension at 72° C. for 1.5 minutes; and final elongation at 70° C. for 7 minutes.

After the PCR experiment was completed, 0.8% agarose gel electrophoresis was employed to verify whether a PCR product having a size of about 1408 bps was obtained. The verified PCR product was purified and recovered from the agarose gel by virtue of gel Advance™ gel extraction system. Afterward, Genomics Biosci & Tech (Taipei, Taiwan) was requested to conduct sequencing for the purified PCR product. The sequencing result confirms that the PCR product has a nucleotide sequence as shown in SEQ ID NO:3. The nucleotide sequence of the PCR product was uploaded to the NCBI website such that an accession number of GU576971.1 was obtained. The Blastx program at the NCBI website was used to deduce an amino acid sequence encoded by the nucleotide sequence of the PCR product. The deduced amino acid sequence was subjected to comparison analysis using the protein database at the NCBI website.

Results:

The nucleotide sequence (NCBI Accession No. GU576971.1) of the aforementioned PCR product obtained according to this invention was deduced to have an amino acid sequence as shown in SEQ ID NO:4 using the Blastx program at the NCBI website. After the deduced amino acid sequence was subjected to the comparison analysis using the protein database at the NCBI website, it is found that: the deduced amino acid sequence has 87%, 78%, and 98% sequence identities to the amino acid sequences of pancreatic lipases belonging to *Homo sapiens, Mus musculus*, and *Sus scrofa*, respectively. The applicants accordingly presumed that: the nucleotide sequence (SEQ ID NO:3) of the PCR product obtained according to this invention is certainly able to encode porcine pancreatic lipase; nucleotide residues 1-4 and nucleotide residues 1403-1408 constitute non-coding sequences; nucleotide residues 5-1399 constitute the complete coding sequence (named pLip gene) of porcine pancreatic lipase; and a stop codon is at nucleotide positions 1400-1402. The porcine pancreatic lipase (SEQ ID NO:4) encoded by pLip gene has 465 amino acids. Regarding the porcine pancreatic lipase, the $1^{st}$-$16^{th}$ amino acid residues from the N-terminus constitute a signal peptide (encoded by nucleotide residues 5-52 of the aforementioned PCR products), and the $17^{th}$-$465^{th}$ amino acid residues from the N-terminus constitute a mature peptide (SEQ ID NO:5, encoded by nucleotide residues 53-1399 of the aforementioned PCR products).

Example 2

Expression of Porcine Pancreatic Lipase Gene (pLip Gene) in *Pichia pastoris* GS115

A. Construction of pGem-pLip Recombinant Vector

The PCR product (1408 bps) having pLip gene as obtained in section B of the above Example 1 was used as a template, and a primer pair, pLip-U and pLip-D, was designed based on nucleotide residues 50-67 and nucleotide residues 1383-1398 of the aforesaid PCR product, so as to be used in a PCR experiment having reaction conditions as shown in Table 2. The nucleotide sequences of pLip-U primer and pLip-D primer are shown below. Therefore, a DNA fragment (1362 bps) having pLip gene was amplified via the PCR experiment. Due to the design of the primer pair, the DNA fragment having pLip gene possesses a nucleotide sequence encoding the $16^{th}$ amino acid residue (i.e., glycine, Gly) of the aforementioned signal peptide and a nucleotide sequence (SEQ ID NO: 6) encoding the entire aforementioned mature peptide.

```
pLip-U primer
5'-gaattcggaagcgaagtctgtttc-3'   (SEQ ID NO: 7)
   EcoRI pLip-D primer
5'-ttctagacacggtgtgagggtga-3'    (SEQ ID NO: 8)
   XbaI
```

The two primers as described above were respectively designed to have restriction sites (see the underlined portions) for restriction enzymes EcoRI and XbaI.

TABLE 2

Reaction conditions used in PCR experiment

| Content | Volume (μL) |
|---|---|
| PCR product obtained in section B of Example 1 (0.2 μg/μL) | 1 |
| pLip-U primer (0.5 μM) | 1 |
| pLip-D primer (0.5 μM) | 1 |
| dNTPs (10 mM) | 1 |
| Taq DNA polymerase buffer (10X) | 5 |
| Platinum ® Taq DNA polymerase High Fidelity (5 U/μL) | 0.2 |
| MgSO$_4$ (50 mM) | 2 |
| deionized water | 38.8 |

Operating conditions: denaturation at 94° C. for 2 minutes; followed by 30 cycles of the following reactions: denaturation at 94° C. for 30 seconds, primer annealing at 65° C. for 30 seconds, and elongation/extension at 72° C. for 1.5 minutes; and final elongation at 70° C. for 7 minutes.

After the PCR experiment was accomplished, 0.8% agarose gel electrophoresis was utilized to verify whether a PCR product having a size of about 1362 bps was acquired. The verified PCR product was purified and recovered from the agarose gel using gel Advance™ gel extraction system. Subsequently, the purified PCR product was incorporated into pGEM T-Easy vector to perform TA cloning, thereby forming pGEM-pLip recombinant vector. Open reading frame of the resultant pGEM-pLip recombinant vector was confirmed via nucleotide sequencing. The confirmed pGEM-pLip recombinant vector was used to conduct the following experiment.

B. Construction of pGAPZα A-pLip Recombinant Vector

The pGEM-pLip recombinant vector as obtained in the preceding section, entitled "A. Construction of pGEM-pLip recombinant vector", and pGAPZα A vector were utilized to construct pGAPZα A-pLip recombinant vector. pGAPZα A vector (3147 bps) is a *Pichia* expression vector and has the following characteristics:

1. pGAPZα A vector has a GAP promoter ($P_{GAP}$), is able to drive expression of the target gene in *Pichia*, and can be targeted to GAP locus of *Pichia* for homologous recombination, thereby forming a stable transformant.

2. pGAPZα A vector carries an α-factor signal sequence. Therefore, a protein product expressed by virtue of pGAPZα A vector has an α-factor signal peptide at the N-terminus thereof and hence can be secreted out of a host cell.

3. pGAPZα A vector has restriction sites for restriction enzymes EcoRI, XbaI, and BglII.

4. pGAPZα A vector has Zeocin resistance gene for transformant selection.

5. The protein product expressed by virtue of pGAPZα A vector carries a c-myc epitope at the C-terminus thereof so that the protein product can be detected using anti-myc antibody.

Figure 1:
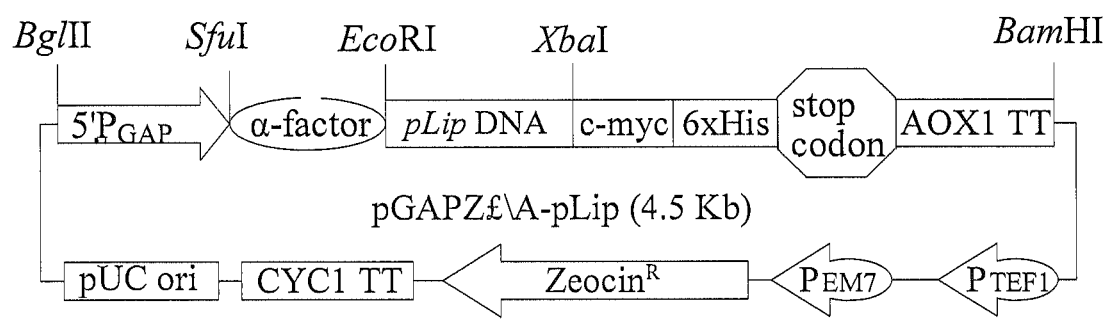
FIG. 1 is a schematic map of pGAPZαA-pLip recombinant vector constructed by pGAPZαA vector and a DNA fragment encoding pLip gene, in which 5'-$P_{GAP}$ represents a 5'-GAP promoter; c-myc represents a c-myc epitope; 6×His represents a histidine hexamer; AOX1 TT represents AOX1 transcription terminator; $P_{TEF1}$ represents a TEF1 promoter; $P_{EM7}$ represents an EM7 promoter; Zeocin$^R$ represents Zeocin resistance gene; CYC1 TT represents a CYC1 transcription terminator; pUCori represents a pUC origin of replication; and EcoRI, XbaI, BglII, SfuI and BamHI represent restriction sites for the corresponding restriction enzymes.

FIG. 1 is the schematic map of pGAPZα A-pLip recombinant vector. How pGAPZα A-pLip recombinant vector was constructed is briefly described as follows. A DNA fragment having a size of 3084 bps (i.e., a carrier DNA) was excised from pGAPZα A vector with restriction enzymes EcoRI/XbaI. In addition, a DNA fragment having a size of 1355 bps and possessing pLip gene (i.e., an insert DNA) was excised from pGEM-pLip recombinant vector using restriction enzymes EcoRI/XbaI. Subsequently, the carrier DNA and the insert DNA were subjected to ligation in a molar ratio of 1 to 3 using T4 DNA ligase, thereby forming pGAPZα A-pLip recombinant vector (4439 bps).

C. Transformation of *Pichia pastoris* GS115 Using pGAPZα A-pLip Recombinant Vector Transformation of *Pichia pastoris* GS115 was conducted by dint of electroporation. First, *Pichia pastoris* GS115 was inoculated into YPD broth, followed by cultivation in a shaking incubator (30° C., 250 rpm). When a cell density of about 1.3-1.5 ($OD_{600}$) was reached (i.e., about $5\times10^7$ cells/mL), 50 mL of the culture was subjected to centrifugation at 3000 g for 10 minutes. After supernatant was removed, sterile water was used to wash cell pellets twice. Afterward, 1.5 mL of ice-cold 1 M sorbitol was employed to sufficiently suspend cells, thereby forming a cell suspension. Furthermore, the pGAPZα A-pLip recombinant vector as obtained in the preceding section, entitled "B. Construction of pGAPZα A-pLip recombinant vector" was cut using restriction enzyme BglII such that linearized pGAPZα A-pLip recombinant vector was formed.

100 μL of the cell suspension and 10 μg of the linearized pGAPZα A-pLip recombinant vector were uniformly mixed. The resultant mixture was then transferred to an ice-cold 2-mm electroporation cuvette. *Pichia pastoris* GS115 in the resultant mixture was electroporated using Gene Pulser (Bio-Rad, Hercules, Calif.) according to the following parameters: 1,500 V, 25 μF, and 200Ω. The electroporated *Pichia pastoris* GS115 was cultivated at 30° C. for 1 hour. The resultant culture was spread on YPDS solid agar plates containing 1 M sorbitol and 100 μg/mL Zeocin, followed by conducting cultivation at 30° C. for 2-3 days so as to select Zeocin-resistant colonies. Subsequently, Zeocin-resistant colonies were picked, and were subjected to three rounds of selection by sequentially cultivating in YPDS solid agar plates having 500 μg/mL, 1000 μg/mL, and 2000 μg/mL Zeocin. Consequently, multicopy *Pichia* pastoris GS115 transformants were acquired. Additionally, 100 μL of the cell suspension and 10 μg of linearized pGAPZα A vector formed via cutting of restriction enzyme BglII were evenly mixed, followed by conducting the same procedures for transforming *Pichia pastoris* GS115. Thus, *Pichia pastoris* GS115 transformant containing the pGAPZα A vector was also obtained and was used as the negative control.

In order to confirm that pGAPZα A-pLip recombinant vector was successfully integrated into genomic DNA of *Pichia pastoris* GS115 transformants, the applicants randomly picked 11 strains of *Pichia pastoris* GS115 transformants containing pGAPZα A-pLip recombinant vector and 1 strain of *Pichia pastoris* GS115 transformant containing pGAPZα A vector for the following experiment.

First, the aforementioned *Pichia pastoris* GS115 transformants were subjected to extraction of genomic DNA using High Pure PCR Template Preparation Kit according to the manufacturer's instructions. Afterward, the thus obtained genomic DNA served as templates, and a specific primer pair for pLip gene as shown in Table 3 was utilized to conduct a PCR experiment. Furthermore, α-tubulin gene was used as an internal control. The reaction conditions and the operating conditions of the PCR experiments are respectively shown in Tables 4 and 5.

TABLE 3

Primers used in PCR experiments

| Target gene | Primer | Nucleotide Sequence (5'→3') | Size of PCR product (bp) |
|---|---|---|---|
| pLip | pGAP F | gtccctatttcaatcaattg aa (SEQ ID NO: 9) | 1832 |

TABLE 3-continued

Primers used in PCR experiments

| Target gene | Primer | Nucleotide Sequence (5'→3') | Size of PCR product (bp) |
|---|---|---|---|
| | 3' AOX1 | gcaaatggcattctgacatcc (SEQ ID NO: 10) | |
| α-tubulin | α-tubulin-F | agatggccgaccaatgtgacg (SEQ ID NO: 11) | 220 |
| | α-tubulin-R | tgttccagggtggtatgcgtg (SEQ ID NO: 12) | |

TABLE 4

Reaction conditions of PCR experiments

| Content | Volume (μL) |
|---|---|
| genomic DNA (0.1 μg/μL) | 1 |
| forward primer (0.5 μM) | 1 |
| reverse primer (0.5 μM) | 1 |
| dNTPs (10 mM) | 1 |
| Taq DNA polymerase buffer (10X) | 5 |
| Platinum ® Taq DNA polymerase High Fidelity (5 U/μL) | 0.2 |
| MgSO$_4$ (50 mM) | 2 |
| deionized water | 38.8 |

TABLE 5

Operating conditions of PCR experiments

| Gene | Operating conditions |
|---|---|
| pLip | denaturation at 94° C. for 2 minutes; followed by 30 cycles of the following reactions: denaturation at 94° C. for 0.5 minute, primer annealing at 58° C. for 0.5 minute, and elongation/extension at 72° C. for 1.5 minutes; and final elongation at 72° C. for 7 minutes. |
| α-tubulin | denaturation at 94° C. for 2 minutes; followed by 30 cycles of the following reactions: denaturation at 94° C. for 0.5 minute, primer annealing at 60° C. for 0.5 minute, and elongation/extension at 72° C. for 0.5 minute; and final elongation at 72° C. for 7 minutes. |

After the PCR experiments were completed, 0.8% agarose gel electrophoresis was used to verify whether a PCR product having a size of about 1832 bps was obtained, thereby confirming whether pGAPZα A-pLip recombinant vector was successfully integrated into the genomic DNA of *Pichia pastoris* GS115 transformants.

Figure 2:
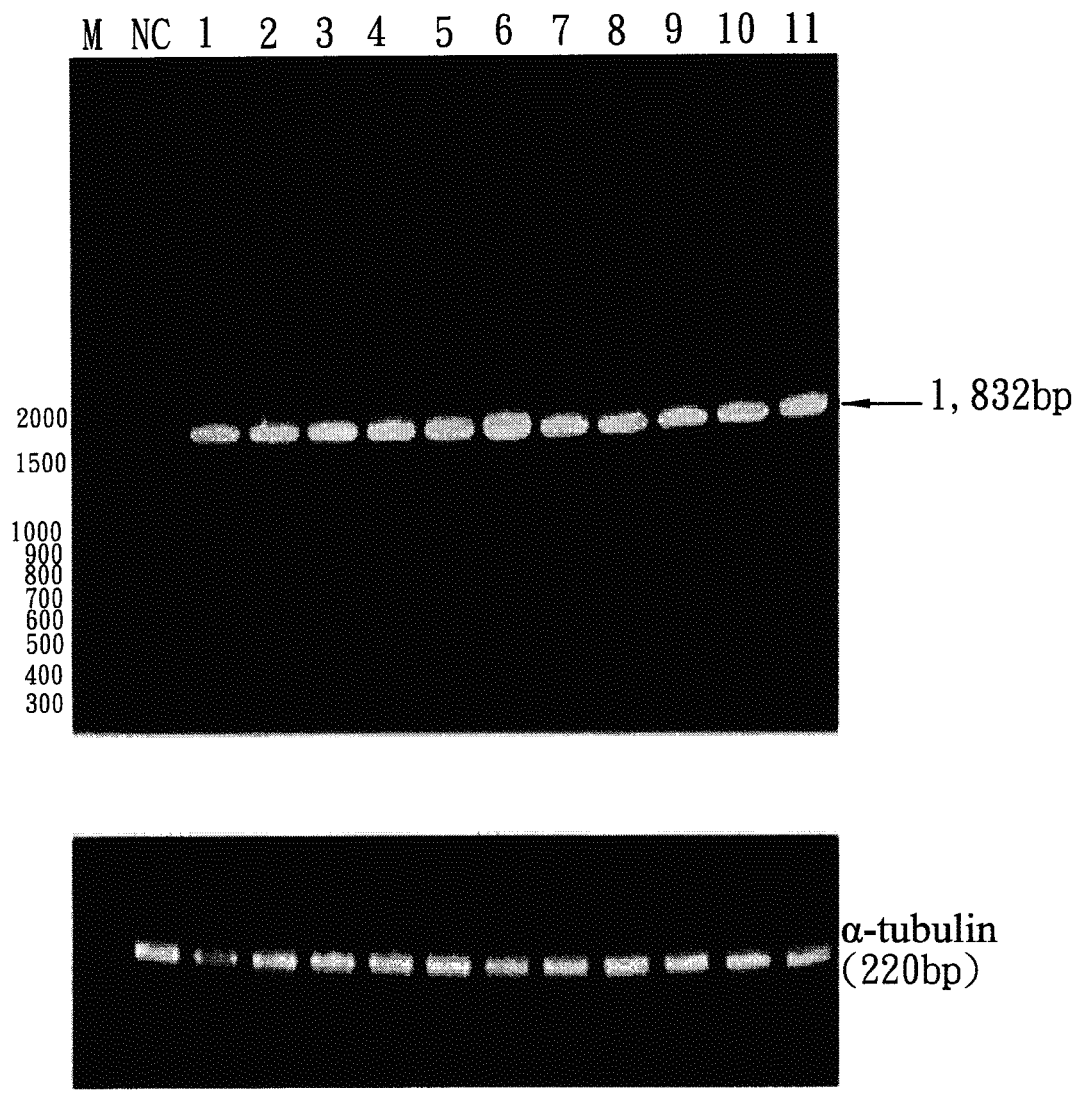
FIG. 2 shows the results of agarose gel electrophoresis of PCR products as obtained from PCR experiments using the primer pairs shown in Table 3, in which lane M shows the DNA ladder markers; lane NC (negative control) shows the result of the *Pichia pastoris* GS115 transformant containing pGAPZαA vector; lanes 1-11 respectively show the results of *Pichia pastoris* GS115 transformants 1-11 containing pGAPZαA-pLip recombinant vector; and the α-tubulin gene serves as an internal control.

Results:

FIG. 2 shows the results of agarose gel electrophoresis of the PCR products as obtained from the PCR experiments using the primer pairs shown in Table 3, in which lane M shows the DNA ladder markers; lane NC (negative control) shows the result of the *Pichia pastoris* GS115 transformant containing pGAPZα A vector; lanes 1-11 respectively show the results of *Pichia pastoris* GS115 transformants 1-11 containing pGAPZα A-pLip recombinant vector; and the α-tubulin gene served as the internal control. As shown in FIG. 2, compared to the negative control, a PCR product having a size of about 1832 bps was amplified from the genomic DNA of each of *Pichia pastoris* GS115 transformants 1-11 containing pGAPZα A-pLip recombinant vector. These experimental results reveal that pGAPZα A-pLip recombinant vector was successfully integrated into GAP locus of each of the *Pichia pastoris* GS115 transformants.

Example 3

Selection of *Pichia pastoris* GS115 Transformants Containing pGAPZα A-pLip Recombinant Vector and Having High Transcriptional Efficiency

*Pichia pastoris* GS115 transformants 1-11 containing pGAPZα A-pLip recombinant vector as selected in the above Example 2 and the *Pichia pastoris* GS115 transformant containing pGAPZα A vector (the negative control) were inoculated into YPD broth, followed by cultivation in a shaking incubator (30° C., 250 rpm). When a cell density of about 1.3-1.5 (OD$_{600}$) was reached (i.e., about 5×10$^7$ cells/mL), centrifugation at 3000 g and 4° C. for 10 minutes was conducted. After supernatant was removed, 25 U lyticase (Sigma, St. Louis, Mo.) was added into each of cell pellets, followed by gentle shaking in a 30° C. water bath for 30 minutes so as to digest cell walls of *Pichia pastoris*. Accordingly, cell lysates were obtained.

The obtained cell lysates were subjected to total RNA extraction using RNeasy Mini Kit according to the manufacturer's instructions. 1 μg of the acquired total RNA was sufficiently suspended with 15 μL of DEPC-water, followed by adding random hexamer primers. First-strand cDNA was then synthesized using SuperScript™ III First-Strand Synthesis System according to the manufacturer's instructions.

In order to perform a PCR experiment, the above first-strand cDNA was used as a template, and a specific primer pair for pLip gene as shown in Table 6 was employed. Moreover, α-tubulin gene served as an internal control. The reaction conditions and operating conditions of the PCR experiments are respectively shown in Tables 7 and 8.

TABLE 6

Primers used in PCR experiments

| Target gene | Primer | Nucleotide Sequence (5'→3') | Size of PCR product (bp) |
|---|---|---|---|
| pLip | pLip-R(+) | ttattcgcagcatcctccgc (SEQ ID NO: 13) | 1764 |
| | 3' AOX1 | gcaaatggcattctgacatcc (SEQ ID NO: 10) | |
| α-tubulin | α-tubulin-F | agatggccgaccaatgtgacg (SEQ ID NO: 11) | 220 |
| | α-tubulin-R | tgttccagggtggtatgcgtg (SEQ ID NO: 12) | |

TABLE 7

Reaction conditions of PCR experiments

| Content | Volume (μL) |
|---|---|
| first-strand cDNA (0.1 μg/μL) | 1 |
| forward primer (0.5 μM) | 1 |
| reverse primer (0.5 μM) | 1 |
| dNTPs (10 mM) | 1 |
| Taq DNA polymerase buffer (10X) | 5 |

TABLE 7-continued

Reaction conditions of PCR experiments

| Content | Volume (μL) |
|---|---|
| Platinum ® Taq DNA polymerase High Fidelity (5 U/μL) | 0.2 |
| MgSO$_4$ (50 mM) | 2 |
| deionized water | 38.8 |

TABLE 8

Operating conditions of PCR experiments

| Gene | Operating conditions |
|---|---|
| pLip | denaturation at 94° C. for 2 minutes; followed by 25 cycles of the following reactions: denaturation at 94° C. for 1 minute, primer annealing at 55° C. for 2 minutes, and elongation/extension at 72° C. for 2 minutes; and final elongation at 72° C. for 7 minutes. |
| α-tubulin | denaturation at 94° C. for 2 minutes; followed by 30 cycles of the following reactions: denaturation at 94° C. for 0.5 minute, primer annealing at 60° C. for 0.5 minute, and elongation/extension at 72° C. for 0.5 minute; and final elongation at 72° C. for 7 minutes. |

After the PCR experiments were accomplished, 0.8% agarose gel electrophoresis was utilized to verify whether a PCR product having a size of about 1764 bps and the partial pLip gene was acquired. The gels were stained with ethidium bromide (EtBr), followed by observation under a UV lamp. The results are shown in FIG. 3.

The bands on the gels were subjected to densitometric analysis using SmartSpec™ Plus spectrophotometer (Biorad, Cat. No. 170-2525). The PCR product of first-strand cDNA synthesized from mRNA encoded by α-tubulin gene was used as a control gene for normalization. An optical density ratio of a respective one of the PCR products containing the partial pLip gene to the PCR product of α-tubulin gene was calculated. The optical density ratio of the PCR product of *Pichia pastoris* GS115 transformant 11 to the PCR product of α-tubulin gene (i.e., the lowest optical density ratio) was adjusted to 100%. The relative percentages of the optical density ratios regarding the remaining PCR products of *Pichia pastoris* GS115 transformants 1-10 were calculated based on the optical density ratio and the adjusted percentage regarding the PCR product of *Pichia pastoris* GS115 transformant 11. The calculated results are expressed as mean±SD (n=3) in FIG. 4.

Figure 3:
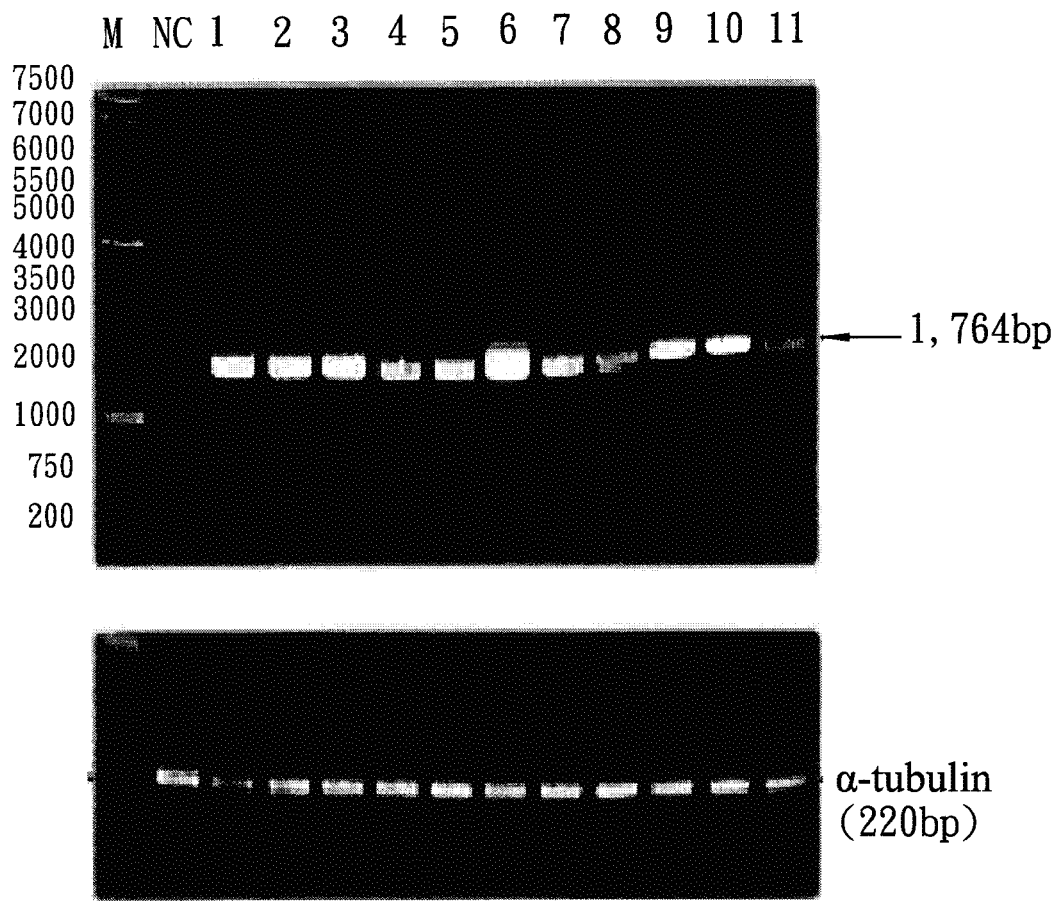
FIG. 3 shows the results of agarose gel electrophoresis of PCR products as obtained from PCR experiments utilizing the primer pairs as shown in Table 6, in which lane M shows the DNA ladder markers; lane NC (negative control) shows the result of the *Pichia pastoris* GS115 transformant containing pGAPZα A vector; lanes 1-11 respectively show the results of *Pichia pastoris* GS115 transformants 1-11 containing pGAPZα A-pLip recombinant vector; and the PCR product of the first-strand DNA synthesized from mRNA encoded by α-tubulin gene serves as an internal control.

Results:

FIG. 3 shows the results of agarose gel electrophoresis of the PCR products as obtained from the PCR experiments utilizing the primer pairs as shown in Table 6, in which lane M shows the DNA ladder markers; lane NC (negative control) shows the result of the *Pichia pastoris* GS115 transformant containing pGAPZα A vector; lanes 1-11 respectively show the results of *Pichia pastoris* GS115 transformants 1-11 containing pGAPZα A-pLip recombinant vector; and the PCR product of the first-strand cDNA synthesized from mRNA encoded by α-tubulin gene was used as the internal control. As shown in FIG. 3, compared to the negative control, a PCR product having a size of about 1764 bps was amplified from the first-strand cDNA of each of *Pichia pastoris* GS115 transformants 1-11 containing pGAPZα A-pLip recombinant vector.

Figure 4:
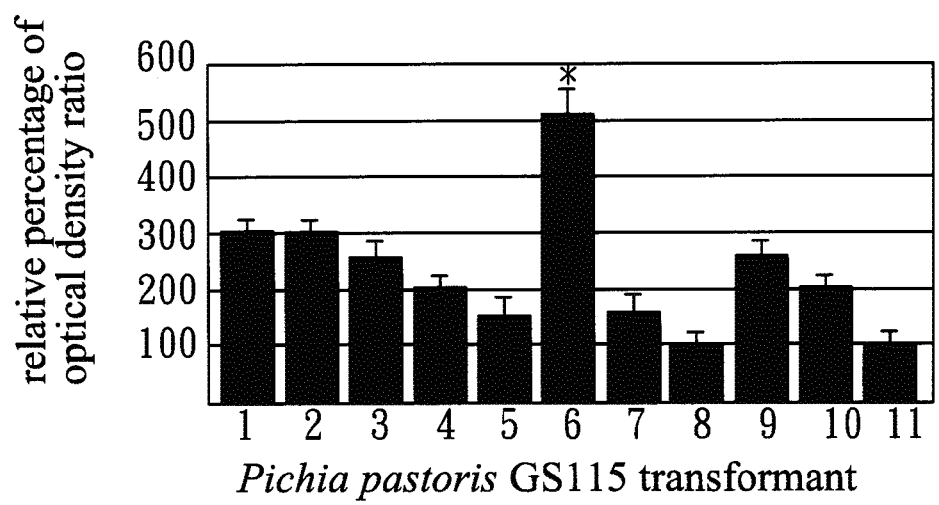
FIG. 4 is a bar chart showing the results as obtained by conducting the densitometric analysis on expression of pLip genes of *Pichia pastoris* GS115 transformants 1-11 containing pGAPZα A-pLip recombinant vector with SmartSpec™ Plus spectrophotometer, in which the symbol "*" represents p<0.05.

FIG. 4 is a bar chart showing the results as obtained by conducting the densitometric analysis on expression of pLip genes of *Pichia pastoris* GS115 transformants 1-11 containing pGAPZα A-pLip recombinant vector with SmartSpec™ Plus spectrophotometer. As shown in FIG. 4, compared to the optical density ratio and the adjusted percentage regarding the PCR product of *Pichia pastoris* GS115 transformant 11, the relative percentage of the optical density ratio regarding *Pichia pastoris* GS115 transformant 6 is about 500% (namely, expression of pLip gene thereof is the highest), and the relative percentage of the optical density ratio regarding *Pichia pastoris* GS115 transformant 8 is about 100% (namely, expression of pLip gene thereof is equal to that of *Pichia pastoris* GS115 transformant 11, and is the lowest). These experimental results manifest that: each of *Pichia pastoris* GS115 transformants 1-11 containing pGAPZα A-pLip recombinant vector according to this invention is capable of effectively transcribing pLip gene into porcine pancreatic lipase mRNA; and *Pichia pastoris* GS115 transformant 6 has the highest transcriptional efficiency.

Example 4

Production of Recombinant Porcine Pancreatic Lipase Using *Pichia pastoris* GS115 Transformant According to this Invention In order to further understand the ability of the *Pichia pastoris* GS115 transformants containing pGAPZα A-pLip recombinant vector according to this invention to express recombinant porcine pancreatic lipase, the following experiments were performed using *Pichia pastoris* GS115 transformants 6 and 8 which respectively have the highest and the lowest transcriptional efficiency of pLip gene.

A. Expression of Recombinant Porcine Pancreatic Lipase

*Pichia pastoris* GS115 transformants 6 and 8 were inoculated into YPD broth, followed by cultivation in a shaking incubator (30° C., 250 rpm) for 72 hours. The resultant culture was subjected to centrifugation at 3000 g and 4° C. for 10 minutes, followed by collecting supernatant so as to filter the same using Centriprep YM-10 (Amicon, Danvers, Mass.). Therefore, a filtrate containing recombinant porcine pancreatic lipase was obtained and was used as a protein sample. In addition, the *Pichia pastoris* GS115 transformant containing pGAPZα A vector as obtained in the above Example 2 was utilized as a negative control and was subjected to the same procedures.

B. Polyacrylamide Gel Electrophoresis (PAGE) and Western Blotting

Figure 5:
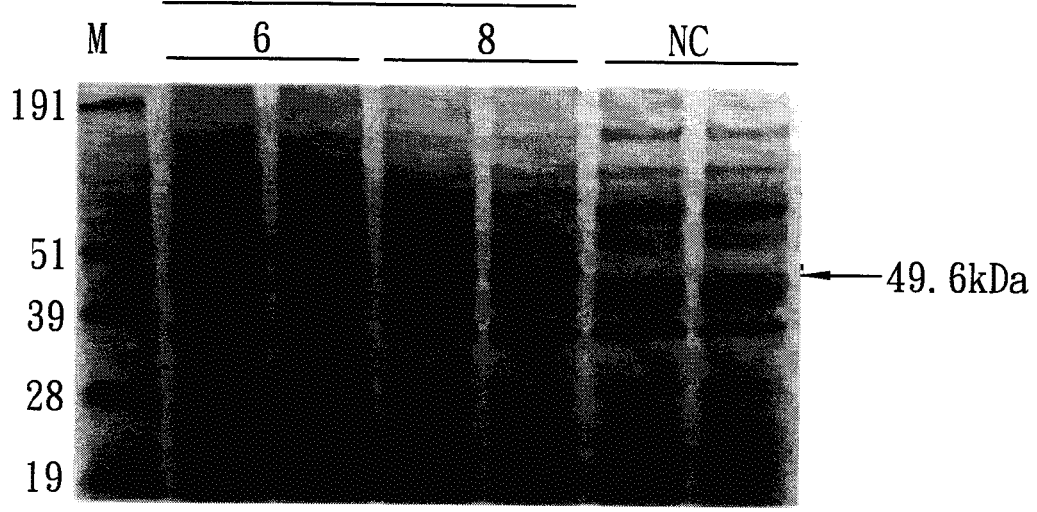
FIG. 5 is a protein electrophoretogram showing the detection of the recombinant porcine pancreatic lipase in the filtrates as obtained from the cultures formed by cultivating *Pichia pastoris* GS115 transformants 6 and 8 for 72 hours, in which lane M shows the protein ladder markers; lanes NC (negative control) show the protein sample of the *Pichia*

PAGE was conducted via Xcell SureLock™ Mini-cell. First, 10 μg of each of the protein samples as obtained from the preceding section, entitled "A. Expression of recombinant porcine pancreatic lipase", was loaded into a respective one of sample wells of a 4-12% NuPAGE® Novex Bis-Tris Gel. Afterward, PAGE was run under reducing conditions using NuPAGE® MES SDS running buffer and a voltage of 200 V for about 0.5 hour. The gel was stained with SimplyBlue™ Safestain according to the manufacturer's instructions. The stained gel was rinsed using ddH$_2$O until the background color of the gel was transparent. The experimental result is shown in FIG. 5.

Additionally, 10 μg of each of the protein samples as obtained from the preceding section, entitled "A. Expression of recombinant porcine pancreatic lipase", was subjected to the same PAGE procedures, but the staining procedure was not conducted. The separated proteins were transferred from the resultant gel onto an immobile-P$^{SQ}$ polyvinylidene difluoride (PVDF) membrane (Millipore, Bedford, Mass.) using XCell II™ Blot Module (Invitrogen, Cat. No. E19051). The transfer was run at a current of 500 mA for 16 hours. The blotted PVDF membrane was acquired and was subjected to a blocking treatment at the room temperature by virtue of 5% (w/v) skim milk [in PBST (99.5% PBS, 0.05% Tween-20)] for 1 hour, followed by washing with PBST three times (10 minutes for each time). Mouse anti-myc monoclonal antibody serving as the primary antibody (diluted 3000-fold with PBST containing 0.1% BSA) was added. After a 16-hour reaction at 4° C., PBST was used to wash three times (10 minutes for each time). Goat anti-mouse IgG-HRP antibody serving as the secondary antibody (diluted 3000-fold with PBST containing 0.1% BSA) was added. After one-hour reaction at the room temperature, PBST was employed to wash three times (10 minutes for each time).

Finally, the PVDF membrane was visualized by virtue of an enhanced chemiluminescence detection system (Amersham Pharmacia Biotech., Arlington Heights, Ill.). The PVDF membrane was exposed to Amersham Hyperfilm ECL (20.3× 25.4 cm, GE Healthcare) for one minute. The film was then developed using a developer solution (Kodak). The experimental result is shown in FIG. 6.

Results:

FIG. 5 is a protein electrophoretogram showing the detection of the recombinant porcine pancreatic lipase in the filtrates as obtained from the cultures formed by cultivating *Pichia pastoris* GS115 transformants 6 and 8 for 72 hours, in which lane M shows the protein ladder markers; lanes NC (negative control) show the protein sample of the *Pichia pastoris* GS115 transformant containing pGAPZα A vector; and lanes 6 and 8 respectively show the protein samples of *Pichia pastoris* GS115 transformants 6 and 8 containing pGAPZα A-pLip recombinant vector. As shown in FIG. 5, compared to the negative control, each of *Pichia pastoris* GS115 transformants 6 and 8 according to this invention is able to express recombinant porcine pancreatic lipase having a molecular weight of about 49.6 kDa. In particular, the expression level of recombinant porcine pancreatic lipase in *Pichia pastoris* GS115 transformant 6 is higher than that in *Pichia pastoris* GS115 transformant 8. Furthermore, these experimental results also verify that: recombinant porcine pancreatic lipase produced according to this invention has an α-factor signal peptide at the N-terminus thereof and can be therefore secreted out of the cell.

FIG. 6 is a Western blot showing the immunodetection of recombinant porcine pancreatic lipase produced by *Pichia pastoris* GS115 transformants 6 and 8 using mouse anti-myc monoclonal antibody, in which lane M shows the immunodetection result of the protein ladder markers; lanes NC (negative control) show the immunodetection result of the protein sample of the *Pichia pastoris* GS115 transformant containing pGAPZα A vector; and lanes 6 and 8 respectively show the immunodetection results of the protein samples of *Pichia pastoris* GS115 transformants 6 and 8 containing pGAPZα A-pLip recombinant vector. As shown in FIG. 6, compared to the negative control, recombinant porcine pancreatic lipase expressed in each of *Pichia pastoris* GS115 transformants 6 and 8 according to this invention carries a c-myc epitope at the C-terminus thereof and can be hence detected using anti-myc antibody.

Example 5

Effect of Cultivation Time on Production of Recombinant Porcine Pancreatic Lipase by *Pichia pastoris* GS115 Transformant of this Invention In order to investigate effect of cultivation time on expression level and activity of recombinant porcine pancreatic lipase produced by *Pichia pastoris* GS115 transformants containing pGAPZα A-pLip recombinant vector, *Pichia pastoris* GS115 transformant 6 having the highest expression level of pLip gene was used for the following experiment.

A. Effect of Different Cultivation Times on Expression Level of Recombinant Porcine Pancreatic Lipase

*Pichia pastoris* GS115 transformant 6 was inoculated into YPD broth, followed by cultivation in a shaking incubator (30° C., 250 rpm). A suitable amount of the culture was obtained at 36, 48, 60, 72, 84, and 96 hrs of cultivation. The obtained culture was subjected to centrifugation at 3000 g and 4° C. for 10 minutes. Supernatant was then collected and was subjected to filtration via Centriprep YM-10 (Amicon, Danvers, Mass.). Consequently, a filtrate containing recombinant porcine pancreatic lipase was acquired and was utilized as a protein sample. Equal amounts of the protein samples obtained at the aforesaid different time points were subjected to PAGE according to the method as described in the section, entitled "B. Polyacrylamide gel electrophoresis (PAGE) and Western blotting", of the above Example 4. The experimental result is shown in FIG. 7.

B. Effect of Different Cultivation Times on Activity of Recombinant Porcine Pancreatic Lipase This experiment was performed generally according to the method as described in the preceding section, entitled "A. Effect of different cultivation times on expression level of recombinant porcine pancreatic lipase", except that a suitable amount of the culture to be formed would be obtained at 24, 48, 72, and 96 hrs of cultivation so as to be subjected to the following activity assay.

The activity assay for recombinant porcine pancreatic lipase was conducted generally according to the pH titration method as described in a report by Gaskin et al., *J. Clin. Invest.* (1982), 69:427-434 (i.e., some portions of the pH titration method were modified). Specifically, 0.5 mL of tributyrin (Sigma) serving as an enzyme substrate was added into an assay solution containing 20 mL of 150 mM NaCl, 4 mL of 2 mM Tris-HCl, and 5 mL of 1 mM $CaCl_2$ (pH 8.5), followed by mixing uniformly. Subsequently, 4 mM sodium taurodeoxycholate (NaTDC), 0.3 mL of a respective one of the protein samples, and 50 pmole of colipase (Sigma) were added, followed by mixing uniformly. pH value of the resultant mixture (30 mL) was adjusted to 6.5 using 0.1 M HCl. Afterward, titration for the resultant mixture was conducted at 25° C. for 5 minutes using 0.05 M NaOH such that the pH value of the thus titrated mixture was 8.0.

In this activity assay, one unit of recombinant porcine pancreatic lipase activity is defined as 1 μmole of free butyric acid released from tributyrin in 1 minute at 25° C. Recombinant porcine pancreatic lipase activity in the filtrate formed from the culture obtained at the respective cultivation time of *Pichia pastoris* GS115 transformant 6 can be calculated by substituting the amount of NaOH added for titration into the following formula:

$$A = (B \times 0.05 \times 3.33 \times 10^6)/(5 \times 10^3) \quad (1)$$

where A=recombinant porcine pancreatic lipase activity (U)
B=amount of 0.05 M NaOH added for titration (mL)
The experimental results are shown in Table 9.

Results:

FIG. 7 is a protein electrophoretogram showing the expression level of recombinant porcine pancreatic lipase in the filtrate formed from the culture obtained at the respective cultivation time (36 hrs, 48 hrs, 60 hrs, 72 hrs, 84 hrs, or 96 hrs) of *Pichia pastoris* GS115 transformant 6, in which lane M shows the protein ladder markers. As shown in FIG. 7, during the entire period of cultivation, *Pichia pastoris* GS115 transformant 6 according to this invention is able to stably express recombinant porcine pancreatic lipase.

TABLE 9

Recombinant porcine pancreatic lipase activity at different cultivation times

| Cultivation time (hours) | Recombinant porcine pancreatic lipase activity (U/300 μL) |
|---|---|
| 24 | 102.2 |
| 48 | 180.3 |
| 72 | 300.4 |
| 96 | 305.8 |

Referring to Table 9, under suitable cultivation conditions, *Pichia pastoris* GS115 transformant 6 according to this invention is capable of producing recombinant porcine pancreatic lipase and secreting the same therefrom, and recombinant porcine pancreatic lipase activity increases with the cultivation time since the expression level of recombinant porcine pancreatic lipase also increases with the cultivation time. After 72 hours of cultivation, recombinant porcine pancreatic lipase activity tends to be steady.

Example 6

Evaluation of Ability of Recombinant Porcine Pancreatic Lipase of this Invention to Enhance Growth Performance and Fat Utilization of Postweaning Piglet A. Experimental Animal 48 LYD three-breed piglets (at the age of 28 days, a body weight of about 7.8 kg), which were purchased from Animal Industry Division, Livestock Research Institute, Council of Agriculture, Taiwan, were used in the following experiment. The experimental animals were randomly divided into three groups including two experimental groups (i.e., porcine pancreatic lipase groups 1 and 2) and a control group. The experimental animals were randomly placed in 24 pens, each of which has a size of 4 m², and sufficient water and feeds were supplied to the experimental animals. The experimental animals were raised under the guidelines of Animal Care Committee of the Council of Agriculture, Taiwan.

B. Effect of Mixed Feed Containing Recombinant Porcine Pancreatic Lipase According to this Invention on Growth Performance of Postweaning Piglet A large number of *Pichia pastoris* GS115 transformant 6 was inoculated into YPD broth, followed by cultivation in a shaking incubator (29° C., 250 rpm) for 72 hours. The resultant culture was subjected to centrifugation at 4° C. and 3000 g for 10 minutes. Supernatant was collected and was subjected to filtration using Milligard® Cartridge Filter (Millipore). Subsequently, the resultant filtrate was condensed by virtue of Pellicon® 2 Filter (Millipore) such that a concentrated solution containing recombinant porcine pancreatic lipase was obtained. Afterward, a suitable amount of glyerol was added into the concentrated solution to reach a final concentration of 5%. Thus, activity of recombinant porcine pancreatic lipase could be protected when a subsequent freeze-drying process is conducted. The dried recombinant porcine pancreatic lipase was dissolved in 0.1% Triton X-100, followed by performing activity assay according to the method as described in the section, entitled "B. Effect of different cultivation times on activity of recombinant porcine pancreatic lipase", of the above Example 5. The recombinant porcine pancreatic lipase analyzed by virtue of the enzyme activity assay was used to formulate a feed.

Each of the experimental piglets was fed with a mixed feed for 42 days after postweaning. The mixed feed supplied to each group of postweaning piglets was made from a basal diet and a blend, and was formulated according to the ingredients as shown in Table 10. Moreover, composition of the mixed feed for each group of the postweaning piglets is shown in Table 11. Formulation of the blend for each group of the postweaning piglets is described as follows. Each of the blends used for making the mixed feeds supplied to porcine pancreatic lipase groups 1 and 2 was formulated by blending a suitable amount of yellow corn (as a carrier), and a respective one of the 5000 U/kg (for porcine pancreatic lipase group 1) and 10000 U/kg (for porcine pancreatic lipase group 2) dried recombinant porcine pancreatic lipase. Additionally, the blend used for making the mixed feed supplied to the control group was formulated by blending a suitable amount of yellow corn and a dried product containing pGAPZα A vector. Specifically, the dried product containing pGAPZα A vector is formed by first subjecting the culture of the *Pichia pastoris* GS115 transformant containing pGAPZα A vector to centrifugation, filtration, and condensation, and secondly freeze-drying the resultant concentrated solution.

TABLE 10

Ingredients of mixed feed supplied to each group of postweaning piglets

| | Ingredients | Control group | Porcine pancreatic lipase group 1 Content (%) | Porcine pancreatic lipase group 2 |
|---|---|---|---|---|
| basal diet | yellow corn | 67.65 | 67.75 | 67.69 |
| | 44% soybean meal | 19.0 | 19.0 | 19.0 |
| | 35% dried skim milk | 2.0 | 1.93 | 1.86 |
| | dried whey | 2.0 | 2.0 | 2.0 |
| | 61.2% fish meal | 5.0 | 5.0 | 5.0 |
| | dicalcium phosphate | 1.6 | 1.6 | 1.6 |
| | pulverized limestone | 0.80 | 0.80 | 0.80 |
| | iodized salt | 0.5 | 0.5 | 0.5 |
| | vitamin premix[a] | 0.1 | 0.1 | 0.1 |
| | mineral premix[b] | 0.15 | 0.15 | 0.15 |
| | soybean oil | 1.0 | 1.0 | 1.0 |
| | 50% chloride-choline | 0.1 | 0.1 | 0.1 |
| blend | recombinant porcine pancreatic lipase | — | 0.1 | 0.2 |
| | pGAPZα A vector | 0.1 | — | — |
| | total | 100 | 100 | 100 |

[a]Vitamin premix provided the following vitamins per kg of the basal diet: 8000 IU of vitamin A, 800 IU of vitamin D₃, 30 IU of vitamin E, 1.0 mg of vitamin K₃, 2.0 mg of thiamin, 5.0 mg of riboflavin, 25 μg of vitamin B₁₂, 12 mg of Ca-pantothenate, 18 mg of niacin, 0.4 mg of folic acid, 0.06 mg of biotin, and 120 mg of choline); and
[b]Mineral premix provided the following minerals per kg of the basal diet: 10 mg of Cu, 100 mg of Fe, 100 mg of Zn, 10 mg of Mn, and 0.1 mg of Se.

TABLE 11

Composition of mixed feed supplied to each group of postweaning piglets

| | | Control group | Porcine pancreatic lipase group 1 | Porcine pancreatic lipase group 2 |
|---|---|---|---|---|
| calculated value | crude protein (%) | 18.49 | 18.45 | 18.41 |
| | digestible energy (kcal/kg) | 3550 | 3550 | 3550 |

TABLE 11-continued

Composition of mixed feed supplied to each group of postweaning piglets

|  |  | Control group | Porcine pancreatic lipase group 1 | Porcine pancreatic lipase group 2 |
|---|---|---|---|---|
|  | lysine (%) | 1.19 | 1.18 | 1.20 |
|  | calcium (%) | 0.88 | 0.88 | 0.88 |
|  | phosphorus (%) | 0.69 | 0.69 | 0.69 |
| analyzed | dry matter (%) | 87.77 | 87.67 | 87.37 |
| value | crude protein (%) | 18.52 | 18.59 | 18.56 |
|  | crude fat (%) | 3.48 | 3.53 | 3.58 |

On Days 1, 7, 14, 21, 28, 35, and 42 during supply of the mixed feed, feed intake and the body weight of the postweaning piglets in each group were measured and recorded. Subsequently, average daily gain (ADG) and average daily feed intake (ADFI) of the postweaning piglets in each group were calculated based on the body weight and the feed intake. Feed efficiency (FE) defined as a ratio of ADFI to ADG was also calculated. The experimental results are shown in Table 12.

Furthermore, on Days 1, 7, and 42 during supply of the mixed feed, blood samples were collected from the venous sinuses of the postweaning piglets in each group using 21G needles (0.8×38 mm, BD). EDTA (Sigma) was used as an anticoagulant. Subsequently, centrifugation at 3000 g was conducted for 30 minutes. Accordingly, plasma specimens were obtained and were subjected to the experiment in the following section C.

C. Effect of Mixed Feed Containing Recombinant Porcine Pancreatic Lipase According to this Invention on Triglyceride (TG) and Urea Nitrogen (UN) Concentrations in Plasma of Postweaning Piglet Analysis for TG and UN concentrations in plasma was performed generally according to the method as described in a report by C. M. Hung et al., *Evid. Complement. Alter. Med.* (2009), DOI:10.1093/ecam/nep021 (i.e., some portions of the method in the report were modified). Specifically, the plasma specimens of the postweaning piglets in each group, which were obtained in the preceding section entitled "B. Effect of mixed feed containing recombinant porcine pancreatic lipase according to this invention on growth performance of postweaning piglet", were analyzed by using Triglyceride-GPO Reagent Set and Liquid Urea Nitrogen (BUN) Reagent Set according to the manufacturer's instructions, and by utilizing automation and wet type system of blood biochemistry analyzer (HITACHI 7040 Model). The experimental results are shown in Table 13.

D. Statistical Analysis

Data were subjected to statistical analysis as a randomized complete block design using SAS General Linear Model procedure (SAS Institute Inc., Cary, N.C.). The results of analysis are expressed as mean values, and mean squared errors (MSE) were calculated. The results were analyzed using least-squares means (LS-Means) so as to assess differences between the three groups. Statistical significance is indicated by $p<0.05$.

Results:

TABLE 12

Effect of mixed feed containing recombinant porcine pancreatic lipase on growth performance of postweaning piglet

| Day of feeding | Control group | Porcine pancreatic lipase group 1 | Porcine pancreatic lipase group 2 | MSE |
|---|---|---|---|---|
| Body weight (kg) | | | | |
| Day 1 | $7.84^a$ | $7.84^a$ | $7.72^a$ | 0.061 |
| Day 7 | $8.67^a$ | $9.36^b$ | $9.36^b$ | 0.106 |
| Day 14 | $10.27^a$ | $11.80^b$ | $11.92^b$ | 0.085 |
| Day 21 | $12.53^a$ | $14.93^b$ | $15.21^b$ | 0.051 |
| Day 28 | $15.72^a$ | $19.04^b$ | $19.22^b$ | 0.102 |
| Day 35 | $19.39^a$ | $23.39^b$ | $23.79^b$ | 0.126 |
| Day 42 | $24.16^a$ | $28.82^b$ | $29.56^b$ | 0.137 |
| ADG (kg) | | | | |
| Days 1-7 | $0.12^a$ | $0.22^b$ | $0.23^b$ | 0.008 |
| Days 8-14 | $0.23^a$ | $0.35^b$ | $0.37^b$ | 0.010 |
| Days 15-21 | $0.32^a$ | $0.45^b$ | $0.47^b$ | 0.009 |
| Days 22-28 | $0.46^a$ | $0.59^b$ | $0.57^b$ | 0.013 |
| Days 29-35 | $0.52^a$ | $0.62^b$ | $0.65^b$ | 0.016 |
| Days 36-42 | $0.68^a$ | $0.78^{ab}$ | $0.82^b$ | 0.020 |
| Days 1-42 (overall period of feeding) | $0.39^a$ | $0.5^b$ | $0.52^b$ | 0.002 |
| ADFI (kg) | | | | |
| Days 1-7 | $0.20^a$ | $0.34^b$ | $0.32^b$ | 0.017 |
| Days 8-14 | $0.42^a$ | $0.55^b$ | $0.54^b$ | 0.016 |
| Days 15-21 | $0.62^a$ | $0.77^a$ | $0.75^a$ | 0.029 |
| Days 22-28 | $0.82^a$ | $0.95^a$ | $0.92^a$ | 0.025 |
| Days 29-35 | $1.03^a$ | $1.05^a$ | $1.11^a$ | 0.019 |
| Days 36-42 | $1.32^a$ | $1.34^{ab}$ | $1.43^b$ | 0.022 |
| Days 1-42 (overall period of feeding) | $0.73^a$ | $0.83^b$ | $0.85^b$ | 0.008 |
| FE (kg/kg) | | | | |
| Days 1-7 | $1.80^a$ | $1.58^a$ | $1.39^a$ | 0.107 |
| Days 8-14 | $1.87^a$ | $1.58^a$ | $1.48^a$ | 0.076 |
| Days 15-21 | $1.94^a$ | $1.73^a$ | $1.61^a$ | 0.091 |
| Days 22-28 | $1.82^a$ | $1.63^a$ | $1.61^a$ | 0.071 |
| Days 29-35 | $1.97^a$ | $1.69^a$ | $1.71^a$ | 0.052 |
| Days 36-42 | $1.93^a$ | $1.72^a$ | $1.75^a$ | 0.046 |
| Days 1-42 (overall period of feeding) | $1.89^b$ | $1.67^a$ | $1.63^a$ | 0.015 |

[a]Within the same row, there is no statistical significance (p > 0.05) between the values labeled by superscript a;
[b]Within the same row, there exists statistical significance (p < 0.05) between the value labeled by superscript b and the value labeled by superscript a; and
[ab]Within the same row, there is no statistical significance (p > 0.05) between the value labeled by superscript ab and the value labeled by superscript a, and between the value labeled by superscript ab and the value labeled by superscript b.

Referring to Table 12, the body weight of the postweaning piglets in each of porcine pancreatic lipase groups 1 and 2 is significantly higher than that of the postweaning piglets in the control group on Days 7, 14, 21, 28, 35, and 42. ADG of the postweaning piglets in each of porcine pancreatic lipase groups 1 and 2 is significantly higher than that of the postweaning piglets in the control group in the periods of Days 1-7, Days 8-14, Days 15-21, Days 22-28, and Days 29-35. In addition, in the period of Days 36-42, considering ADG of the postweaning piglets, a significant difference exists between porcine pancreatic lipase group 2 and the control group. ADFI of the postweaning piglets in each of porcine pancreatic lipase groups 1 and 2 is significantly higher than that of the postweaning piglets in the control group in the periods of Days 1-7 and Days 8-14. In the period of Days 36-42, ADFI of the postweaning piglets in porcine pancreatic lipase group 2 is significantly higher than that of the postweaning piglets in the control group.

In terms of the overall period of feeding, ADG and ADFI of the postweaning piglets in each of porcine pancreatic lipase groups 1 and 2 are respectively significantly higher than ADG and ADFI of the postweaning piglets in the control group, and FE with respect to each of porcine pancreatic lipase groups 1 and 2 is significantly lower (i.e., superior) than FE with respect to the control group. The above experimental results indicate that the mixed feed containing recombinant porcine pancreatic lipase of this invention is able to effectively enhance the growth performance of the postweaning piglets.

TABLE 13

Effect of mixed feed containing recombinant porcine pancreatic lipase on TG and UN concentrations in plasma of postweaning piglet

| Day of feeding | Control group | Porcine pancreatic lipase group 1 | Porcine pancreatic lipase group 2 | MSE |
|---|---|---|---|---|
| Triglyceride (mg/dL) | | | | |
| Day 1 | 33.0$^a$ | 25.5$^a$ | 29.4$^a$ | 2.1 |
| Day 7 | 19.8$^a$ | 25.3$^{ab}$ | 30.9$^b$ | 2.0 |
| Day 42 | 54.3$^a$ | 53.3$^a$ | 55.5$^a$ | 6.3 |
| Urea nitrogen (mg/dL) | | | | |
| Day 1 | 11.4$^a$ | 10.7$^a$ | 11.4$^a$ | 0.6 |
| Day 7 | 13.4$^a$ | 13.0$^a$ | 15.7$^a$ | 0.8 |
| Day 42 | 11.2$^a$ | 11.8$^a$ | 12.5$^a$ | 1.0 |

$^a$Within the same row, there is no statistical significance (p > 0.05) between the values labeled by superscript a;
$^b$Within the same row, there exists statistical significance (p < 0.05) between the value labeled by superscript b and the value labeled by superscript a; and
$^{ab}$Within the same row, there is no statistical significance (p > 0.05) between the value labeled by superscript ab and the value labeled by superscript a, and between the value labeled by superscript ab and the value labeled by superscript b.

Referring to Table 13, TG concentration in plasma of the postweaning piglets in porcine pancreatic lipase group 2 is higher than that in plasma of the postweaning piglets in the control group on Day 7. The aforesaid information reveals that the addition of the 10000 U/kg recombinant porcine pancreatic lipase can facilitate utilization of fats in the mixed feed with respect to postweaning piglets. The applicants hence deduce that facilitation of fat utilization can be achieved when an animal feed containing recombinant porcine pancreatic lipase according to this invention is supplied to pigs in different phases of the growth period.

In view of the foregoing experimental results of this example, it can be verified that: recombinant porcine pancreatic lipase according to this invention is able to effectively facilitate utilization of fats in an animal feed with respect to postweaning piglets, and is also capable of enhancing growth performance of postweaning piglets, thereby being adapted to serve as a feed additive.

Moreover, in terms of UN concentration in plasma of the postweaning piglets, on Days 1, 7, and 42, there is no significant difference among the three groups. Consequently, it is indicated that the addition of recombinant porcine pancreatic lipase does not adversely affect the normal functions of kidneys of the postweaning piglets. Accordingly, the applicants deem that: recombinant porcine pancreatic lipase of this invention is adapted to be added into a feed for a postweaning piglet so as to effectively facilitate utilization and absorption of fats in the feed with respect to the postweaning piglet, and so as to further enhance growth performance of the postweaning piglet.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

What is claimed is:

1. An isolated nucleic acid molecule comprising a cDNA sequence that encodes a polypeptide having the amino acid sequence of SEQ ID NO:4 or 5.

2. The isolated nucleic acid molecule of claim 1, wherein the cDNA sequence is the nucleotide sequence of SEQ ID NO:3.

3. The isolated nucleic acid molecule of claim 1, wherein the cDNA sequence is the nucleotide sequence of SEQ ID NO:6.

4. A recombinant vector comprising a cDNA sequence that encodes a polypeptide having the amino acid sequence of SEQ ID NO:4 or 5, and a promoter operatively connected upstream of the cDNA sequence.

5. The recombinant vector of claim 4, wherein the cDNA sequence encodes a polypeptide having the amino acid sequence of SEQ ID NO:5.

6. The recombinant vector of claim 5, wherein the cDNA sequence has the nucleotide sequence of SEQ ID NO:6.

7. The recombinant vector of claim 4, wherein the promoter is selected from the group consisting of PGAP, PTEF1, and PEM7.

8. The recombinant vector of claim 7, wherein the promoter is PGAP.

9. The recombinant vector of claim 4, further having at least one of the following: a secretion signal coding sequence, an antibiotic-resistance gene, an enhancer sequence, a polyadenylation site, a regulatory sequence, a transcription starting site, a transcription termination site, a ribosome binding site, an RNA splicing site, and a translation termination site.

10. A recombinant host cell comprising the recombinant vector of claim 4.

11. The recombinant host cell of claim 10, wherein the vector has a cDNA sequence that encodes a polypeptide having the amino acid sequence of SEQ ID NO: 5.

12. The recombinant host cell of claim 11, wherein the cDNA sequence has the sequence of SEQ ID NO:6.

13. The recombinant host cell of claim 10, which is selected from the group consisting of a yeast cell, an *Escherichia coli* cell, an insect cell, and a mammalian cell.

14. The recombinant host cell of claim 13, which is a yeast cell.

15. The isolated nucleic acid molecule of claim 1, wherein the polypeptide has the amino acid sequence of SEQ ID NO:4.

16. The isolated nucleic acid molecule of claim 1, wherein the polypeptide has the amino acid sequence of SEQ ID NO:5.

* * * * *